US008764747B2

(12) United States Patent
Cummings et al.

(10) Patent No.: US 8,764,747 B2
(45) Date of Patent: Jul. 1, 2014

(54) ELECTROSURGICAL INSTRUMENT COMPRISING SEQUENTIALLY ACTIVATED ELECTRODES

(75) Inventors: John F. Cummings, Madeira, OH (US); Andrew T. Beckman, Cincinnati, OH (US); Bradley E. White, Cincinnati, OH (US); Christopher J. Schall, Cincinnati, OH (US); Cory G. Kimball, Cincinnati, OH (US); Al Mirel, Redwood City, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1034 days.

(21) Appl. No.: 12/797,844

(22) Filed: Jun. 10, 2010

(65) Prior Publication Data

US 2011/0306973 A1     Dec. 15, 2011

(51) Int. Cl.
*A61B 18/18*     (2006.01)

(52) U.S. Cl.
USPC ............... 606/48; 606/50; 606/45; 606/51; 606/52

(58) Field of Classification Search
USPC ................................ 606/45–52, 205–207
See application file for complete search history.

(56) References Cited

U.S. PATENT DOCUMENTS

| 2,366,274 | A | 1/1945 | Luth et al. |
| 2,458,152 | A | 1/1949 | Eakins |
| 2,510,693 | A | 6/1950 | Green |
| 3,166,971 | A | 1/1965 | Stoecker |
| 3,580,841 | A | 5/1971 | Cadotte et al. |
| 3,703,651 | A | 11/1972 | Blowers |
| 4,005,714 | A | 2/1977 | Hiltebrandt |
| 4,058,126 | A | 11/1977 | Leveen |
| 4,220,154 | A | 9/1980 | Semm |
| 4,237,441 | A | 12/1980 | van Konynenburg et al. |
| 4,281,785 | A | 8/1981 | Brooks |
| 4,304,987 | A | 12/1981 | van Konynenburg |
| 4,545,926 | A | 10/1985 | Fouts, Jr. et al. |
| 4,550,870 | A | 11/1985 | Krumme et al. |
| 4,582,236 | A | 4/1986 | Hirose |

(Continued)

FOREIGN PATENT DOCUMENTS

| DE | 29623113 U1 | 10/1997 |
| DE | 20004812 U1 | 9/2000 |

(Continued)

OTHER PUBLICATIONS

Wright, et al., "Time-Temperature Equivalence of Heat-Induced Changes in Cells and Proteins," Feb. 1998. ASME Journal of Biomechanical Engineering, vol. 120, pp. 22-26.

(Continued)

*Primary Examiner* — Linda Dvorak
*Assistant Examiner* — Amanda Scott

(57) ABSTRACT

An electrosurgical surgical instrument can comprise a handle and an end effector, wherein the end effector can comprise first and second jaws which can be opened and closed to capture tissue therebetween. One or both of the first and second jaws can comprise a plurality of electrodes which can be sequentially activated. The electrodes can be activated in a predetermined order in connection with a cutting member being advanced through the tissue. In various embodiments, the electrodes can be deactivated in a predetermined order. In certain embodiments, the electrodes can be comprised of a positive temperature coefficient material which can allow the electrodes to be sequentially deactivated.

21 Claims, 10 Drawing Sheets

(56) References Cited

U.S. PATENT DOCUMENTS

| | | |
|---|---|---|
| 4,761,871 A | 8/1988 | O'Connor et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,190,541 A | 3/1993 | Abele et al. |
| 5,205,459 A | 4/1993 | Brinkerhoff et al. |
| 5,285,945 A | 2/1994 | Brinkerhoff et al. |
| 5,309,927 A | 5/1994 | Welch |
| 5,318,589 A | 6/1994 | Lichtman |
| 5,387,207 A | 2/1995 | Dyer et al. |
| 5,389,098 A | 2/1995 | Tsuruta et al. |
| 5,395,312 A | 3/1995 | Desai |
| 5,403,312 A * | 4/1995 | Yates et al. ............ 606/50 |
| 5,417,709 A | 5/1995 | Slater |
| 5,428,504 A | 6/1995 | Bhatla |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,618,307 A | 4/1997 | Donlon et al. |
| 5,624,452 A | 4/1997 | Yates |
| 5,647,871 A | 7/1997 | Levine et al. |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,876,401 A | 3/1999 | Schulze et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,483 A | 8/2000 | Palmer et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,055,731 B2 | 6/2006 | Shelton, IV et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,241,294 B2 | 7/2007 | Reschke |
| 7,252,667 B2 | 8/2007 | Moses et al. |
| 7,267,685 B2 | 9/2007 | Butaric et al. |
| 7,287,682 B1 | 10/2007 | Ezzat et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,645,277 B2 | 1/2010 | McClurken et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |

(56) References Cited

U.S. PATENT DOCUMENTS

| | | |
|---|---|---|
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,981,113 B2 | 7/2011 | Truckai et al. |
| 8,020,743 B2 | 9/2011 | Shelton, IV |
| 8,070,036 B1 | 12/2011 | Knodel |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,282,669 B2 | 10/2012 | Gerber et al. |
| 8,292,886 B2 | 10/2012 | Kerr et al. |
| 8,298,232 B2 | 10/2012 | Unger |
| 8,323,310 B2 | 12/2012 | Kingsley |
| 2002/0165541 A1 | 11/2002 | Whitman |
| 2003/0078577 A1* | 4/2003 | Truckai et al. ............... 606/51 |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0033278 A1 | 2/2005 | McClurken et al. |
| 2005/0085809 A1 | 4/2005 | Mucko et al. |
| 2005/0096651 A1* | 5/2005 | Truckai et al. ............... 606/51 |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173813 A1 | 7/2007 | Odom |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0138003 A1 | 5/2009 | Deville et al. |
| 2009/0206140 A1 | 8/2009 | Scheib et al. |
| 2009/0209979 A1* | 8/2009 | Yates et al. ............... 606/143 |
| 2009/0248002 A1 | 10/2009 | Takashino et al. |
| 2009/0320268 A1 | 12/2009 | Cunningham et al. |
| 2009/0326530 A1 | 12/2009 | Orban, III et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0264093 A1* | 10/2011 | Schall ............... 606/52 |
| 2011/0276057 A1 | 11/2011 | Conlon et al. |
| 2011/0282339 A1 | 11/2011 | Weizman et al. |
| 2011/0301605 A1 | 12/2011 | Horner |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |
| 2012/0136353 A1 | 5/2012 | Romero |
| 2012/0150176 A1 | 6/2012 | Weizman |
| 2013/0023875 A1 | 1/2013 | Harris et al. |
| 2013/0053831 A1 | 2/2013 | Johnson et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |

(56) References Cited

FOREIGN PATENT DOCUMENTS

| | | |
|---|---|---|
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/089717 A1 | 7/2011 |
| WO | WO 03/001986 A2 | 1/2013 |

OTHER PUBLICATIONS

International Preliminary Report on Patentability for PCT/US2011/039708, Dec. 10, 2012 (8 pages).

International Search Report for PCT/US2011/039708, Aug. 30, 2011 (4 pages).

U.S. Appl. No. 13/221,410, filed Aug. 30, 2011.

U.S. Appl. No. 13/189,169, filed Jul. 22, 2011.

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, Engineering Formulas § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, Integrated Circuit Engineering, Addison-Wesley Publishing, Reading, MA (1979). (book—not attached).

U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.

(56) References Cited

OTHER PUBLICATIONS

U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.

\* cited by examiner

ELECTROSURGICAL INSTRUMENT COMPRISING SEQUENTIALLY ACTIVATED ELECTRODES

BACKGROUND

1. Field of the Invention

The present invention relates to medical devices and methods. More particularly, the present invention relates to electrosurgical instruments and methods for sealing and transecting tissue.

2. Description of the Related Art

In various open, endoscopic, and/or laparoscopic surgeries, for example, it may be necessary to coagulate, seal, and/or fuse tissue. One means of sealing tissue relies upon the application of electrical energy to tissue captured within an end effector of a surgical instrument in order to cause thermal effects within the tissue. Various mono-polar and bi-polar radio frequency (Rf) surgical instruments and surgical techniques have been developed for such purposes. In general, the delivery of Rf energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

In certain arrangements of a bi-polar radiofrequency (Rf) surgical instrument, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate various aspects of the related art in the field of the invention at the time, and should not be taken as a disavowal of claim scope.

SUMMARY

In at least one form, a surgical instrument can comprise a handle comprising a trigger, and, in addition, a shaft extending from the handle, wherein the shaft comprises a firing member operably coupled with the trigger, wherein the firing member is sequentially movable between an initial position, a first deployed position, and a second deployed position, and wherein an actuation of the trigger is configured to impart a firing motion to the firing member and move the firing member between the initial position and the first deployed position and between the first deployed position and the second deployed position. The surgical instrument can further comprise a first conductor, a second conductor, and a return conductor, wherein the return conductor is electrically insulated from the first conductor and the second conductor, and wherein the second conductor is electrically insulated from the first conductor. The surgical instrument can further comprise a cutting member operably coupled with the firing member, and, in addition, an end effector comprising a proximal end operably engaged with the shaft, a distal end, and a first jaw comprising a first electrode comprised of a positive temperature coefficient material, wherein the first conductor is electrically coupled with the first electrode. The end effector can further comprise a second electrode comprised of a positive temperature coefficient material, wherein the first electrode is positioned proximally with respect to the second electrode, and wherein the second conductor is electrically coupled with the second electrode, and, in addition, a second jaw, wherein one of the first jaw and the second jaw is movable relative to the other of the first jaw and the second jaw, wherein the second jaw further comprises a return electrode, and wherein the return conductor is electrically coupled to the return electrode. The surgical instrument can further comprise a controller configured to, one, electrically couple the first conductor with a power source when the firing member is moved into the first deployed position, and, two, electrically couple the second conductor with a power source when the firing member is moved into the second deployed position.

In at least one form, a surgical instrument can comprise a handle comprising a trigger, and, in addition, a shaft extending from the handle, wherein the shaft comprises a firing member operably coupled with the trigger, wherein the firing member is sequentially movable between an initial position, a first deployed position, and a second deployed position, and wherein at least one actuation of the trigger is configured to impart a firing motion to the firing member and move the firing member between the initial position and the first deployed position and between the first deployed position and the second deployed position. The surgical instrument can further comprise a first conductor, a second conductor, wherein the second conductor is electrically insulated from the first conductor, and a cutting member operably coupled with the firing member. The surgical instrument can further comprise an end effector, comprising a proximal end operably engaged with the shaft, a distal end, and a first jaw comprising a first electrode comprised of a positive temperature coefficient material, wherein the first conductor is electrically coupled with the first electrode, and, in addition, a second electrode comprised of a positive temperature coefficient material, wherein the first electrode is positioned proximally with respect to the second electrode, and wherein the second conductor is electrically coupled with the second electrode. The surgical instrument can further comprise a second jaw, wherein one of the first jaw and the second jaw is movable relative to the other of the first jaw and the second jaw, at least one sensor configured to detect when the firing member is in the first deployed position and the second deployed position, and, in addition, a microprocessor configured to, one, electrically couple the first conductor with a power source when the firing member is moved into the first deployed position, and, two, electrically couple the second conductor with a power source when the firing member is moved into the second deployed position.

In at least one form, a surgical instrument can comprise a handle comprising a trigger sequentially movable between an unactuated position, a first actuated position, and a second actuated position, and in addition, a shaft extending from the handle, wherein the shaft comprises a firing member operably coupled with the trigger, wherein the firing member is sequentially movable between an initial position, a first deployed position, and a second deployed position, and wherein at least one actuation of the trigger is configured to impart a firing motion to the firing member and move the firing member between the initial position and the first deployed position and between the first deployed position and the second deployed position. The surgical instrument further comprises a first conductor, a second conductor, wherein the second conductor is electrically insulated from the first conductor, and a cutting member operably coupled with the firing member. The surgical instrument further comprises an end effector comprising a proximal end operably engaged with the shaft, a distal end, and a first jaw, comprising a first electrode, wherein the first conductor is electrically coupled with the first electrode, and, in addition, a second electrode, wherein the first electrode is positioned proximally with respect to the second electrode, and wherein the second conductor is electrically coupled with the second electrode. The surgical instrument further comprises a second jaw, wherein one of the first jaw and the second jaw is movable relative to the other of the first jaw and the second jaw, detection means for detecting the position of one of the trigger and the firing member, and operating means for electrically coupling the first conductor with a power source when one of the trigger is moved into the first actuated position and the firing member is moved into the first deployed position, and for electrically coupling the second conductor with a power source when one of the trigger is moved into the second actuated position and the firing member is moved into the second deployed position.

The foregoing discussion should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
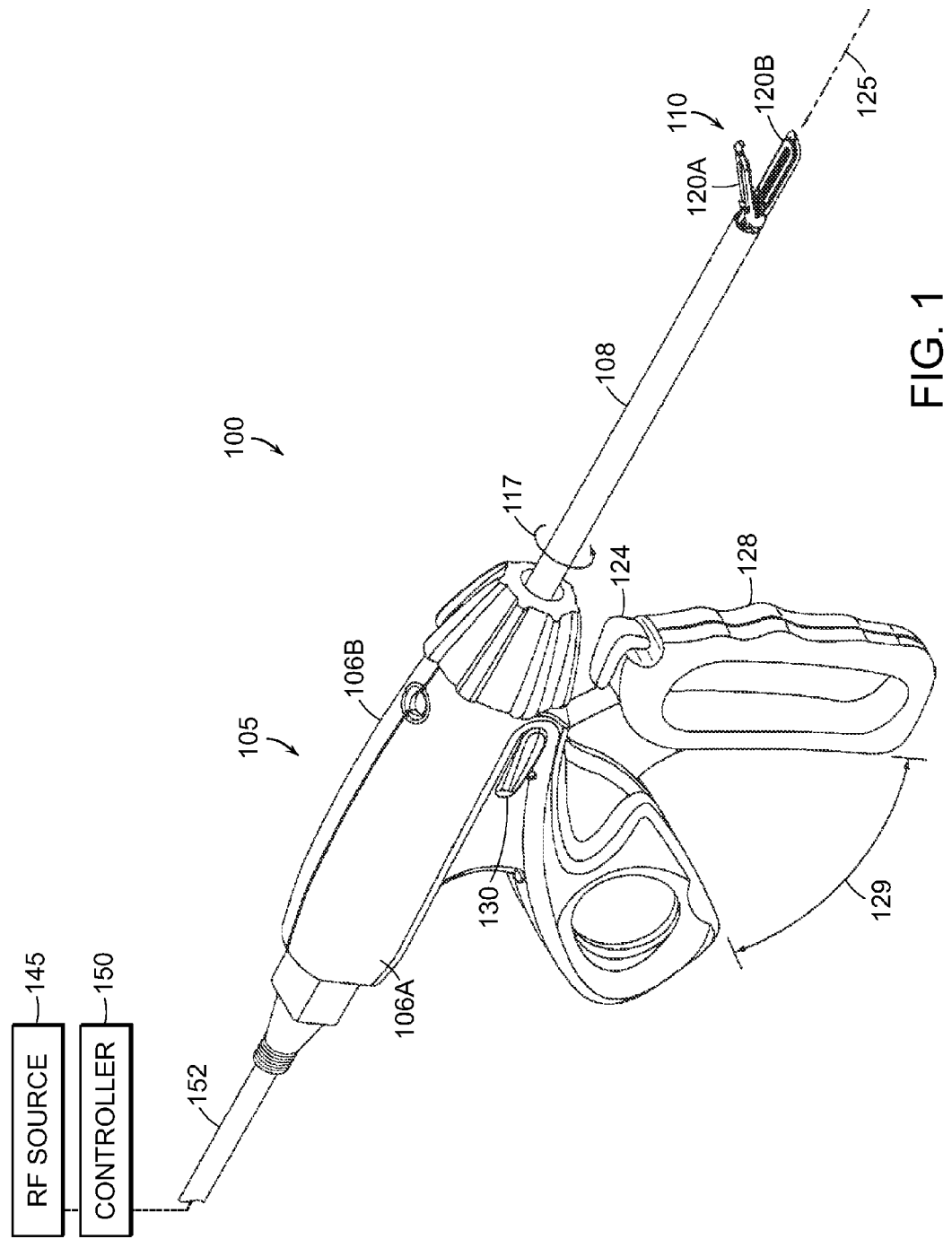
FIG. 1 is a perspective view of an electrosurgical instrument.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

The entire disclosures of the following co-owned non-provisional United States patent applications filed on even date herewith are hereby incorporated by reference herein:

U.S. patent application Ser. No. 12/797,866, entitled HEAT MANAGEMENT CONFIGURATIONS FOR CONTROLLING HEAT DISSIPATION FROM ELECTROSURGICAL INSTRUMENTS;

U.S. patent application Ser. No. 12/797,861, entitled COOLING CONFIGURATIONS FOR ELECTROSURGICAL INSTRUMENTS; and U.S. patent application Ser. No. 12/797,853, entitled ELECTROSURGICAL INSTRUMENT EMPLOYING A THERMAL MANAGEMENT SYSTEM.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may not be fully understood. However, the authors have identified the parameters at which tissue welding can be accomplished. An effective "weld" as disclosed herein results from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

A surgical instrument can be configured to supply energy, such as electrical energy, ultrasonic energy, and/or heat energy, to the tissue of a patient. For example, various embodiments disclosed herein provide electrosurgical jaw structures adapted for transecting captured tissue between the jaws and for contemporaneously welding the captured tissue margins with controlled application of RF energy. In more detail, in various embodiments, referring now to FIG. 1, an electrosurgical instrument 100 is shown. Surgical or electrosurgical instrument 100 can comprise a proximal handle 105, a distal working end or end effector 110 and an introducer or elongate shaft 108 disposed in-between. End effector 110 may comprise a set of openable-closeable jaws with straight or curved jaws—an upper first jaw 120A and a lower second jaw 120B. First jaw 120A and second jaw 120B may each comprise an elongate slot or channel 242 (see FIG. 4A), therein disposed along their respective middle portions along axis 125, for example. First jaw 120A and second jaw 120B may be coupled to an electrical source or RF source 145 and a controller 150 through electrical leads in cable 152. Controller 150 may be used to activate electrical source 145. In various embodiments, the electrical source 145 may comprise an RF source, an ultrasonic source, a direct current source, and/or any other suitable type of electrical energy source, for example.

Figure 2:
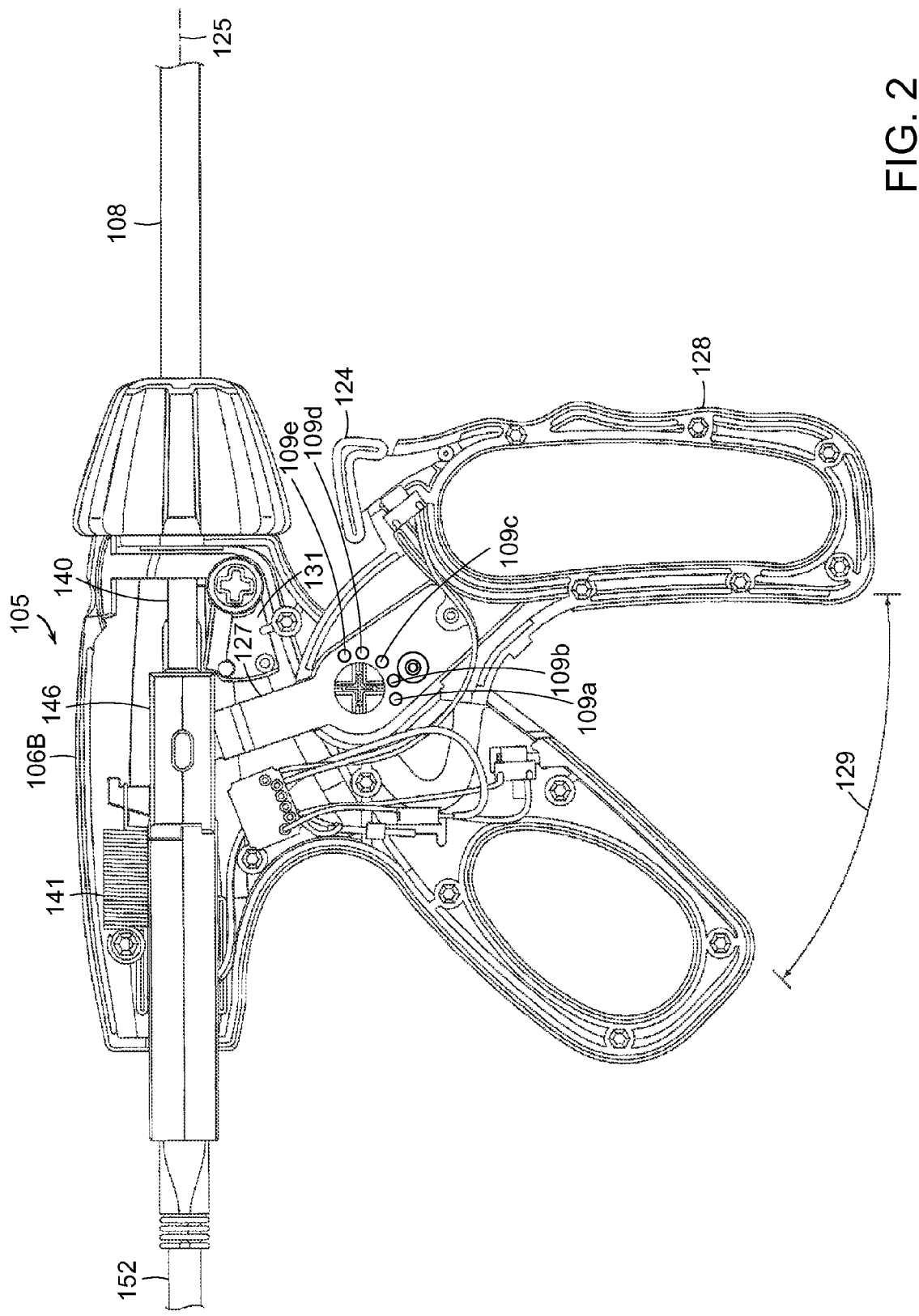
FIG. 2 is a side view of a handle of the surgical instrument of FIG. 1 with a half of a handle body removed to illustrate some of the components therein.

Moving now to FIG. 2, a side view of the handle 105 is shown with half of a first handle body 106A (see FIG. 1) removed to illustrate some of the components within second handle body 106B. Handle 105 may comprise a lever arm 128 which may be pulled along a path 129. Lever arm 128 may be coupled to a movable cutting member disposed within elongate shaft 108 by a shuttle 146 operably engaged to an extension 127 of lever arm 128. The shuttle 146 may further be connected to a biasing device, such as spring 141, for example, which may also be connected to the second handle body 106B, in order to bias the shuttle 146 and thus the cutting member in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers and/or sliders for actuating the first jaw 120A and second jaw 120B. Elongate shaft 108 may have a cylindrical or rectangular cross-section and can comprise a thin-wall tubular sleeve that extends from handle 105. Elongate shaft 108 may include a bore extending therethrough for carrying actuator mechanisms configured to actuate the jaws and/or for carrying electrical leads for delivery of electrical energy to electrosurgical components of end effector 110.

End effector 110 may be adapted for capturing, welding and transecting tissue. First jaw 120A and second jaw 120B may close to thereby capture or engage tissue therebetween. First jaw 120A and second jaw 120B may also apply compression to the tissue. Elongate shaft 108, along with first jaw 120A and second jaw 120B, can be rotated a full 360° degrees, as shown by arrow 117, relative to handle 105 through one or more rotary contacts, for example. First jaw 120A and second jaw 120B can remain openable and/or closeable while rotated. Referring now to FIG. 1, end effector 110 may be coupled to electrical source 145 and controller 150. Controller 150 can regulate the electrical energy delivered by electrical source 145 which in turn delivers electrosurgical energy to electrodes within the jaws 120A, 120B. The energy delivery may be initiated by an activation button 124 operably engaged with lever arm 128 and in electrically communication with controller 150 via cable 152. As mentioned above, the electrosurgical energy delivered by electrical source 145 may comprise radiofrequency (RF) energy. As described in greater detail below, the electrodes of the jaw members may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381, 209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

Figure 3:
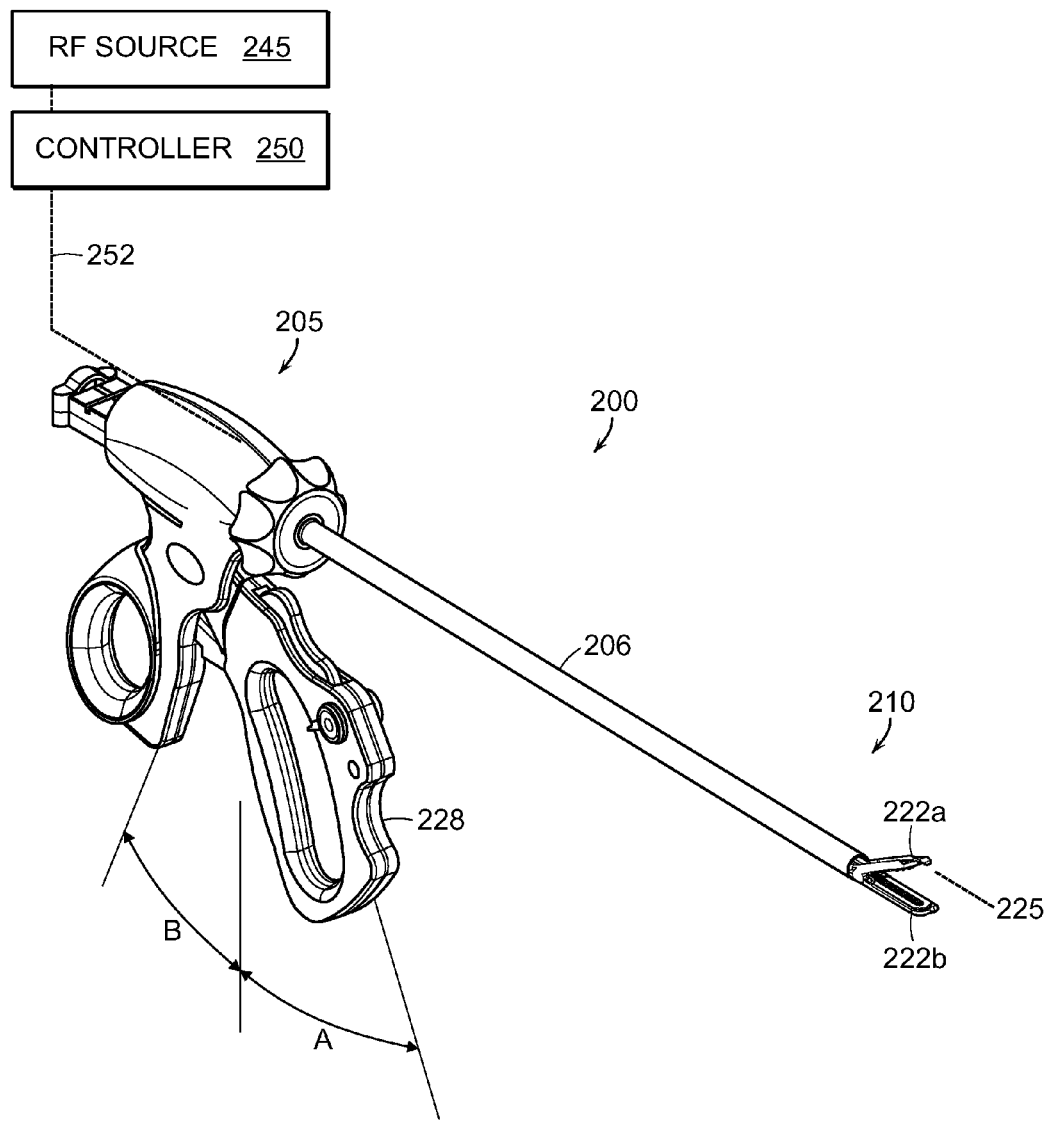
FIG. 3 is a perspective view of an electrosurgical instrument.
Figure 4A:
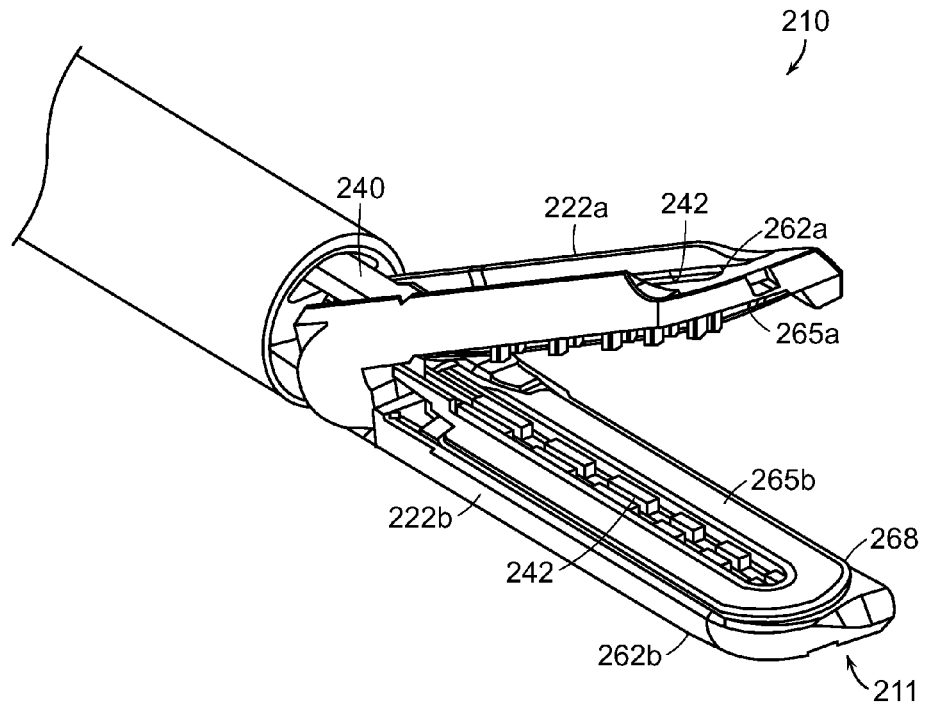
FIG. 4A illustrates an end effector of an electrosurgical instrument in an open configuration.
Figure 4B:
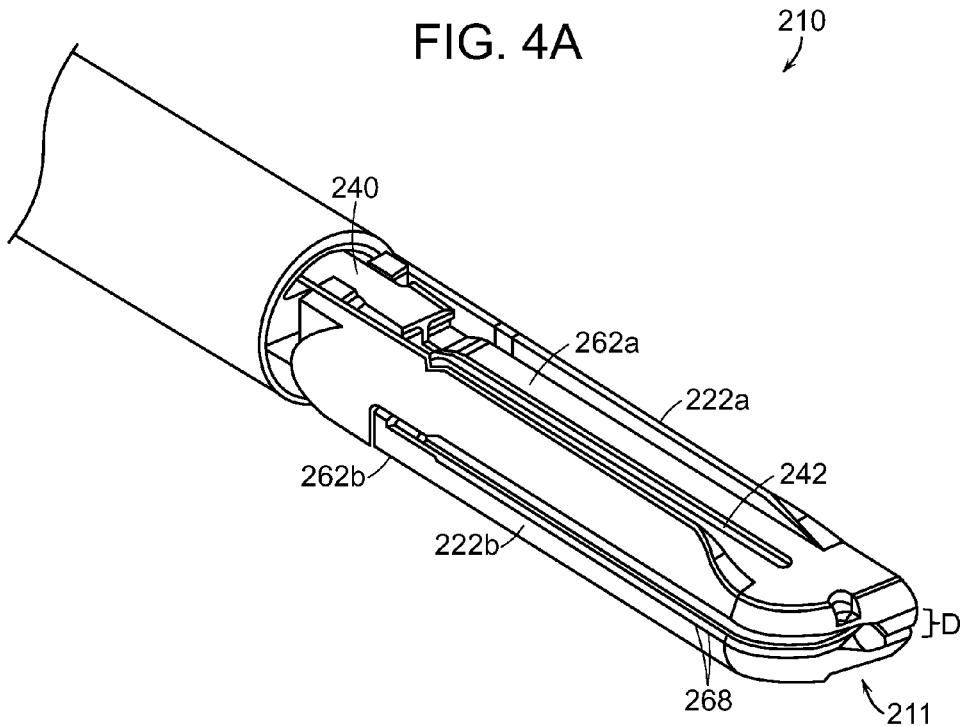
FIG. 4B illustrates the end effector of FIG. 4A in a closed configuration.

FIG. 3 illustrates an electrosurgical instrument 200 comprising a handle end 205, a shaft, or introducer, 206, and an end effector, or working end, 210. Shaft 206 can comprise any suitable cross-section, such as a cylindrical and/or rectangular cross-section, for example, and can comprise a tubular sleeve that extends from handle 205. End effector 210 can extend from shaft 206 and may be adapted for welding and transecting tissue. In various embodiments, end effector 210 can comprise an openable and closeable jaw assembly which can, in various embodiments, comprise straight, curved, and/or any other suitably configured jaws. In various embodiments, the end effector 210 can comprise a first jaw 222*a* and a second jaw 222*b*, wherein at least one of the jaws 222*a* and 222*b* can move relative to the other. In at least one embodiment, the first jaw 222*a* can be pivoted about an axis relative to the second jaw 222*b* in order close onto, capture, and/or engage tissue positioned between the jaws and apply a compression force or pressure thereto. In various embodiments, the handle 205 can comprise a lever arm 228 adapted to actuate a translatable member 240 (FIG. 4A). More particularly, referring to FIGS. 4A and 4B, the lever arm 228 can be actuated in order to move member 240 distally toward the distal end 211 of end effector 210 and, when member 240 is advanced distally, member 240 can contact first jaw 222*a* and move it downwardly toward second jaw 222*b*, as illustrated in FIG. 4B. In at least one embodiment, the translatable member 240 can comprise a proximal rack portion and the lever arm 228 can comprise a plurality of gear teeth which can be configured to drive the proximal rack portion of translatable member 240 distally. In certain embodiments, rotation of the lever arm 228 in the opposite direction can drive the translatable member 240 proximally.

Figure 4C:
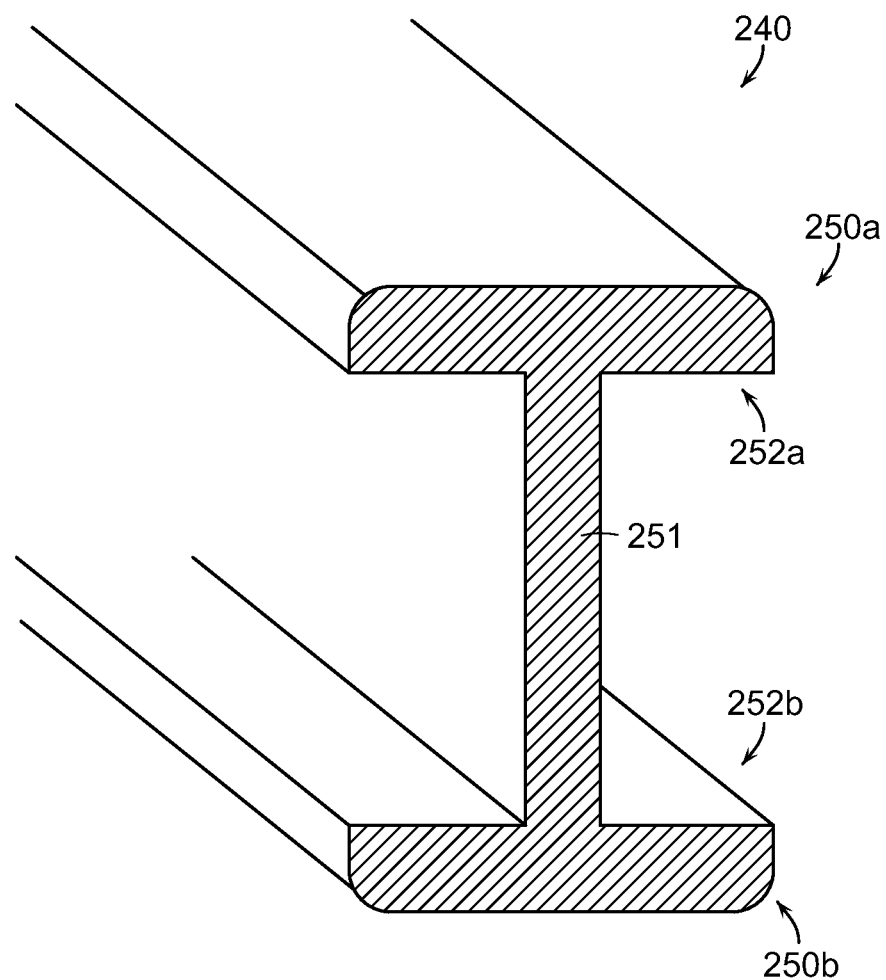
FIG. 4C is a sectional view of a translatable member shaped like an I-beam which is configured to close the end effector of the surgical instrument of FIG. 3.

As described above, the translatable member 240 can be configured to contact first jaw 222*a* and pivot jaw 222*a* toward second jaw 222*b*. In various embodiments, referring now to FIGS. 4A-4C, the distal end of reciprocating member 240 can comprise a flanged "I"-beam configured to slide within a channel 242 in the jaws 222*a* and 222*b*. Referring primarily to FIG. 4C, the I-beam portion of member 240 can comprise an upper flange 250A, a lower flange 250B, and a center, or intermediate, portion 251 connecting the flanges 250A and 250B. In at least one embodiment, the flanges 250A and 250B and the center portion 251 can define "c"-shaped channels on the opposite sides of member 240. In any event, in various embodiments, the flanges 250*a* and 250*b* can define inner cam surfaces 252*a* and 252*b*, respectively, for slidably engaging outward-facing surfaces 262A and 262B of jaws 222*a* and 222*b*, respectively. More particularly, the inner cam surface 252A can comprise a suitable profile configured to slidably engage the outer surface 262A of first jaw 222*a* and, similarly, the inner cam surface 252B can comprise a suitable profile configured to slidably engage the outer surface 262B of second jaw 222*b* such that, as translatable member 240 is advanced distally, the cam surfaces 252A and 252B can co-operate to cam first jaw member 222*a* toward second jaw member 222*b* and configure the end effector 240 in a closed configuration. As seen in FIG. 4B, jaws 222*a* and 222*b* can define a gap, or dimension, D between the first and second electrodes 265A and 265B of jaws 222*a* and 222*b*, respectively, when they are positioned in a closed configuration. In various embodiments, dimension D can equal a distance between approximately 0.0005" to approximately 0.005", for example, and, in at least one embodiment, between approximately 0.001" and approximately 0.002", for example.

As discussed above, the translatable member 240 can be at least partially advanced in order to move the first jaw 222*a* toward the second jaw 222*b*. Thereafter, the movable member 240 can be advanced further distally in order to transect the tissue positioned between the first jaw 222*a* and the second jaw 222*b*. In certain embodiments, the distal, or leading, end of the I-beam portion of 240 can comprise a sharp, or knife, edge which can be configured to incise the tissue. Before, during, and/or after the member 240 is advanced through the tissue, electrical current can be supplied to the electrodes in the first and second jaw members in order to weld the tissue as described in greater detail further below. In various circumstances, the operation of the trigger 228 can advance the knife edge of the cutting member 240 to the very distal end of slot or channel 242. After the cutting member 240 has been sufficiently advanced, the trigger 228 can be released and moved into its original, or unactuated, position in order to retract the cutting member 240 and allow first jaw 222*a* to move into is open position again. In at least one such embodiment, the surgical instrument can comprise a jaw spring configured to bias the first jaw 222*a* into its open position and, in addition, a trigger spring configured to bias the trigger 288 into its unactuated position.

In various embodiments, further to the above, the surgical instrument can comprise a first conductor, such as an insulated wire, for example, which can be operably coupled with the first electrode 265A in first jaw member 222*a* and, in addition, a second conductor, such as an insulated wire, for example, which can be operably coupled with the second electrode 265B in second jaw member 222*b*. In at least one embodiment, referring again to FIGS. 3 and 4A, the first and second conductors can extend through shaft 206 between an electrical connector in handle 205 and the electrodes 265A and 265B in the end effector 210. In use, the first and second conductors can be operably coupled to electrical source 245 and controller 250 by electrical leads in cable 252 in order for the electrodes 265A and 265B to function as paired bi-polar electrodes with a positive polarity (+) and a negative polarity (−). More particularly, in at least one embodiment, one of the first and second electrodes 265A and 265B can be operably coupled with a positive (+) voltage terminal of electrical source 245 and the other of the first and second electrodes 265A and 265B can be electrically coupled with the negative voltage (−) terminal of electrical source 245. Owing to the opposite polarities of electrodes 265A and 265B, current can flow through the tissue positioned between the electrodes 265A and 265B and heat the tissue to a desired temperature. In certain embodiments, the cutting member 240 can act as an electrode when it is electrically coupled to a positive terminal or negative terminal of the source 245, and/or any suitable ground.

As discussed above, a surgical instrument can comprise an end effector including first and second jaws each having one or more electrodes positioned therein. As also discussed above, one or more of such electrodes can be electrically coupled to a power source and polarized such that current can flow between the electrodes. In various embodiments, referring now to FIG. 5, a surgical instrument can comprise an end effector, such as end effector 310, for example, comprising one or more movable jaws. In at least one embodiment, end effector 310 can comprise a first jaw 322a and a second jaw 322b wherein the first jaw 322a is movable relative to the second jaw 322b, although other embodiments are envisioned where the second jaw 322b is movable relative to the first jaw 322a, for example. In various embodiments, referring now to FIG. 8, the first jaw 322a can comprise a first frame 323a and a plurality of electrodes, such as electrodes 364a-364e and 365a-365e, for example, mounted thereto. More particularly, in at least one embodiment, the frame 323a can comprise a plurality of pockets 366 wherein each of the pockets 366 can be configured to receive one of electrodes 364a-364e and 365a-365e therein. In various embodiments, referring again to FIGS. 5 and 6, each of the electrodes 364a-364e and 365a-365e can comprise a mounting portion 367 positioned within a pocket 366 and, in addition, an extended portion 368 extending from the mounting portion 367. In order to electrically insulate the electrodes 364a-364e and the electrodes 365a-365e from one another, the frame 323a can be comprised of an electrically non-conductive or an at least substantially non-conductive insulative material. In addition, the electrodes 364a-364e and 365a-365e can be sufficiently spaced apart from one another such that they are not in contact with one another and/or such that current does not arc between the electrodes 364a-364e and 365a-365e during use.

Figure 5:
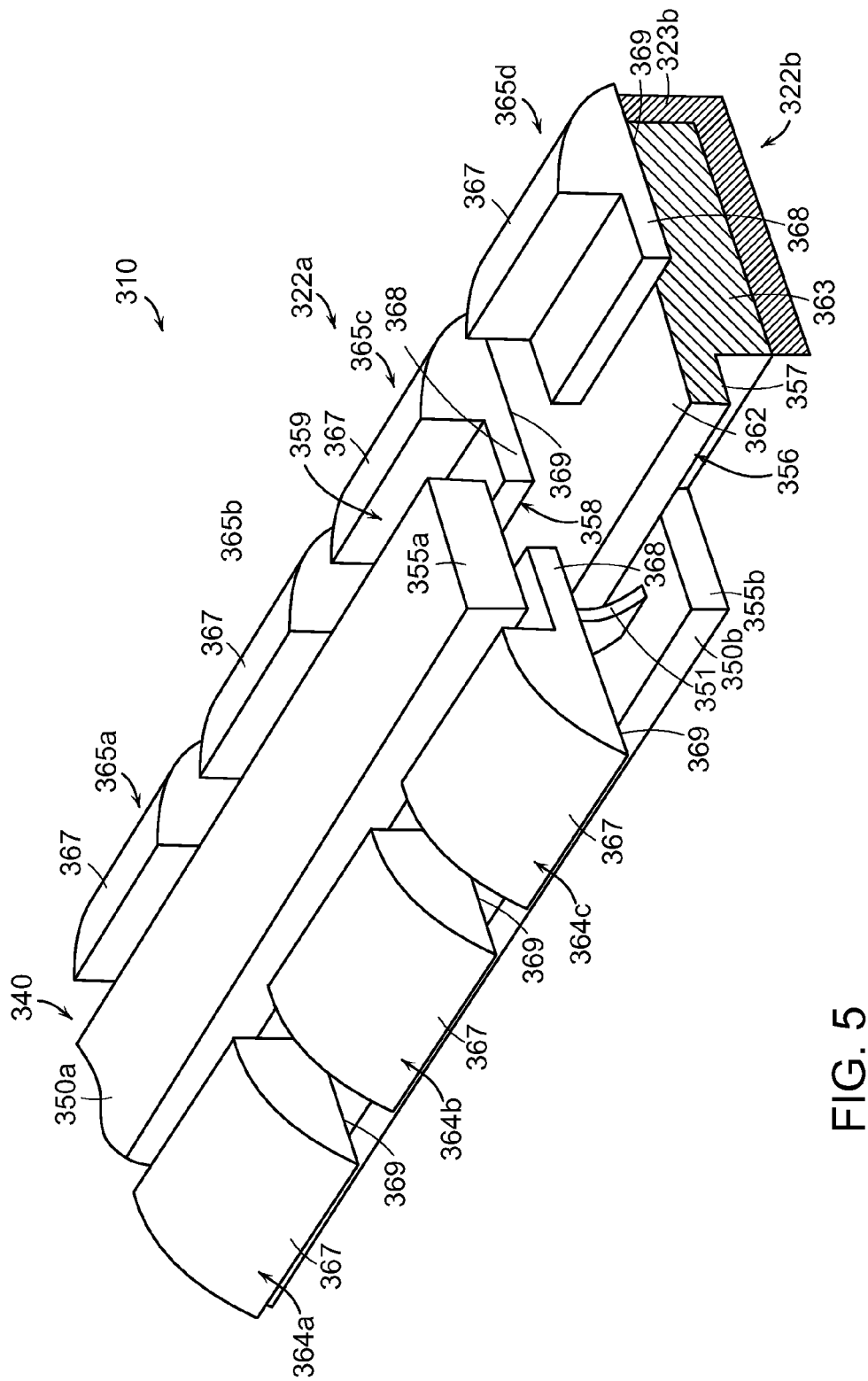
FIG. 5 is a perspective view of an end effector of an electrosurgical instrument illustrated with components removed.
Figure 8:
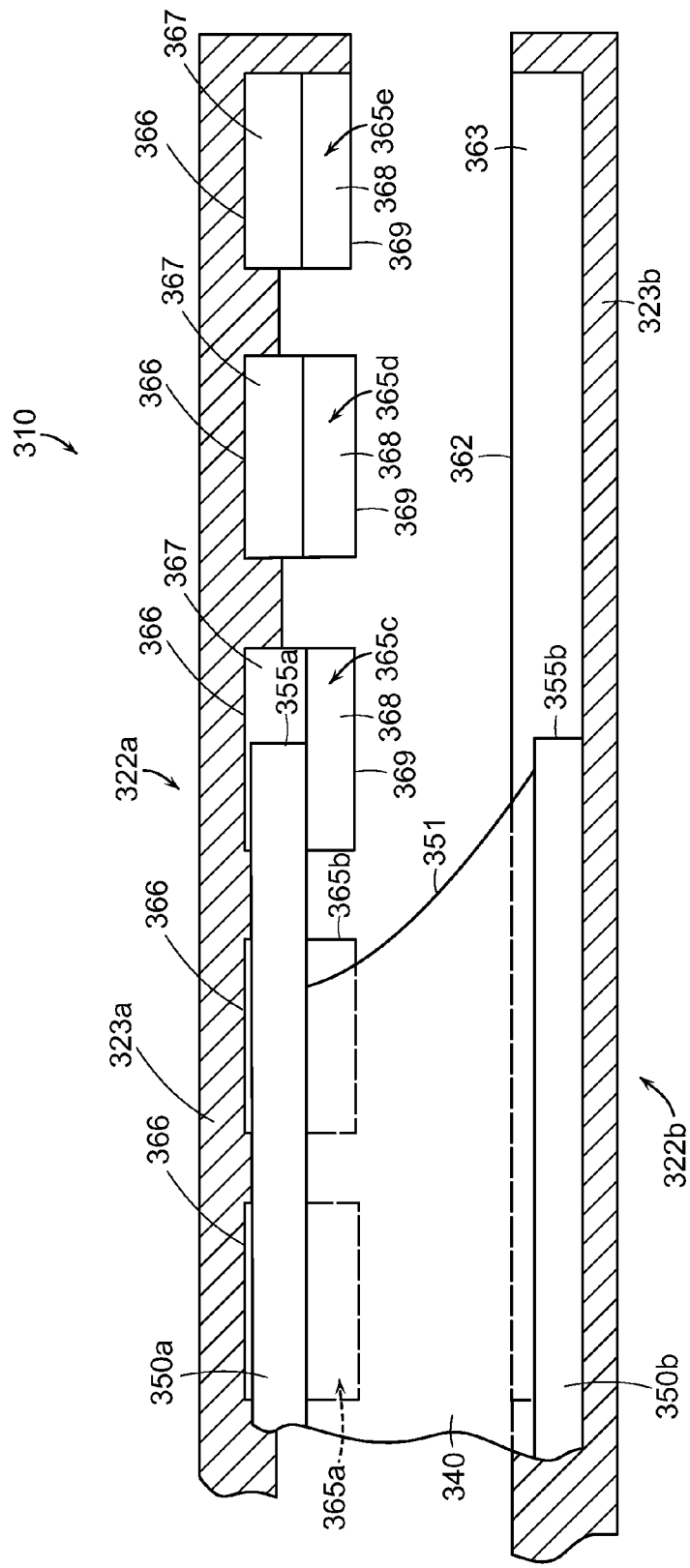
FIG. 8 is a partial cross-sectional view of the end effector of FIG. 5.

In various embodiments, referring now to FIGS. 5 and 8, the second jaw 322b can comprise a second frame 323b and at least one electrode, such as return electrode 363, for example, mounted thereto. In at least one embodiment, the second jaw 322b can comprise a first electrode 363 positioned opposite the electrodes 364a-364e and a second electrode 363 positioned opposite the electrodes 365a-365e. In certain embodiments, the frame 323b can be comprised of an electrically non-conductive, or at least substantially non-conductive, insulative material while, in other embodiments, the second frame 323b can be comprised of an electrically conductive material. In use, as described in greater detail below, current can flow between the electrodes 364a-364e, 365a-365e and the return electrodes 363 when they are electrically coupled with a power source. In various embodiments, further to the above, each of the electrodes 364a-364e, 365a-365e can comprise a tissue-contacting surface 369 which can be positioned against tissue positioned intermediate the first and second jaws 322a, 322b. Similarly, the electrodes 363 can each comprise a tissue-contacting surface 362 which can also be positioned against the tissue. In various embodiments, the tissue-contacting surfaces 362 and 369 can be flat, or at least substantially flat, for example, while, in at least some embodiments, the tissue-contacting surfaces 362 and 369 can comprise one or more arcuate surfaces, for example. In certain embodiments, each of the tissue-contacting surfaces 369 can be co-planar, or at least substantially co-planar, with one another, for example, while, in at least some embodiments, the tissue-contacting surfaces 369 may be parallel, or at least substantially parallel, with one another, for example. In various embodiments, each of the tissue-contacting surfaces 362 can be co-planar, or at least substantially co-planar, with one another, for example, while, in at least some embodiments, the tissue-contacting surfaces 362 may be parallel, or at least substantially parallel, with one another, for example.

In various embodiments, further to the above, the surgical instrument can comprise a firing member, such as cutting member 340, for example, which can be moved relative to the electrodes 363, 364a-364e, and 365a-365e by a trigger, such as trigger 228, for example, in order to, one, compress the tissue-contacting surfaces of such electrodes against the tissue and, two, transect the tissue positioned intermediate the first and second jaws 322a, 322b. Similar to the above, referring now to FIG. 5, the cutting member 340 can comprise a first flange 350a which can be configured to engage the first jaw 322a and, in addition, a second flange 350b which can be configured to engage the second jaw 322b. In certain embodiments, the flanges 350a, 350b of cutting member 340 can be configured to engage the jaws 322a, 322b, respectively, and move the jaws 322a, 322b toward one another as the cutting member 340 is advanced from a proximal position to a distal position within the end effector 310. In certain embodiments, referring again to FIG. 5, the electrodes 364a-364e and the electrodes 365a-365e can define a compression channel, or slot, 359 which can be configured to receive the first flange 350a of cutting member 340 and, in addition, a cutting slot 358 defined between the electrodes 364a-364e and 365a-365e configured to receive a cutting edge 351 extending between the flanges 350a, 350b. In various embodiments, similar to the above, the second jaw 322b can comprise a compression channel, or slot, 357 configured to receive the second flange 350b and, in addition, a cutting slot 356 defined between the electrodes 363 configured to receive the cutting edge 351. In use, in at least one embodiment, the flanges 350a, 350b of cutting member 340 can directly engage the electrodes 364a-364e, 365a-365e and 363 and move the respective tissue-contacting surfaces 362 and 369 toward each other. In certain embodiments, the first flange 350a can comprise a first leading, or compression, portion 355a and the second flange 350b can comprise a second leading, or compression, portion 355b which can be positioned distally with respect to the cutting edge 351.

In various embodiments, the electrodes 364a-364e and 365a-365e can be polarized simultaneously such that current can flow from the electrodes 364a-364e and 365a-365e in the first jaw 322a to the electrodes 363 in the second jaw 322b at the same time. In at least one such embodiment, each of the electrodes 364a-364e and 365a-365e can be polarized with the same, or at least substantially the same, voltage potential while, in other embodiments, the electrodes 364a-364e and 365a-365e can be polarized with different voltage potentials. In various circumstances, the electrodes 364a-364e and 365a-365e can be polarized before the cutting member 340 is advanced relative to the electrodes. In at least some such circumstances, the current flowing between the electrodes can weld the tissue positioned between the jaws 322a, 322b before the tissue is incised. In certain circumstances, the cutting member 340 can be advanced at the same time that current is flowing between the electrodes 364a-364e, 365a-365e and electrodes 363, for example. In various embodiments, the electrodes 364a-364e and 365a-365e can be polarized sequentially. In at least one such embodiment, a first pair of electrodes comprising first electrodes 364a and 365a can be polarized by an RF source, such as RF source 145, for example, such that current can flow between the first electrodes 364a, 365a and the return electrode 363. In certain embodiments, a power source, such as a battery, for example, can be positioned within the handle of the surgical instrument, for example. When the first electrodes 364a and 365a are polarized by the RF source, in various embodiments, the electrodes 364b-364e and 365b-365e may not be polarized by the RF source. In at least one such embodiment, as a result, current may not flow between the electrodes 364b-364e, 365b-365e and electrodes 363 eventhough current may be flowing between the first electrodes 364a, 365a and the electrodes 363. In various embodiments, as described in greater detail below, an electrosurgical instrument can comprise a controller, computer, and/or any suitable microprocessor, such as controller 380 (FIG. 7), for example, which can be configured to selectively electrically couple one or more of the electrodes of end effector 310 with the RF source.

In various embodiments, further to the above, the cutting member 340 can be advanced from a proximal, or initial, position within the end effector 310 to a distal position by the actuation of a trigger, such as trigger 128 (FIG. 2), for example, of the surgical instrument. When the cutting member 340 is in its proximal position, the leading portions 355a, 355b of flanges 350a, 350b, respectively, may not be in contact with the first pair of electrodes 364a, 365a and/or the electrodes 363, for example. In such a proximal position, the first jaw 322a may be in an open configuration and the controller 380 can be programmed such that the electrodes 364a-364e and 365a-365e are electrically uncoupled from the RF source. As the cutting member 340 is advanced distally, the cutting member 340 can be moved into a first distal position in which, one, the leading portion 355a can enter into channel 359 and contact the extended portions 368 of electrodes 364a and 365a and, two, the leading portion 355b can enter into channel 357 and contact the electrodes 363. As described above, the leading portions 355a, 355b can co-operate with another in order to move the first jaw 322a toward the second jaw 322b and compress the tissue therebetween. In at least one embodiment, referring to FIG. 2, the handle 105 of the surgical instrument can comprise at least one sensor which can be configured to detect when the trigger 128 has been actuated sufficiently in order to position the cutting member 340 in its first distal position, for example. In at least one such embodiment, the handle 105 can comprise an encoder sensor which can be configured to detect when a first detectable member 109a on the trigger 328 has passed thereby. In various embodiments, the first detectable member 109a can comprise a colored demarcation, a reflective surface, and/or a magnetic material, such as iron, for example, wherein the encoder sensor can be configured to, one, detect changes in light created by the colored demarcation and/or reflective surface and/or, two, detect disturbances in a magnetic field which are created when the magnetic material passes through the magnetic field produced by the encoder sensor, for example. The encoder sensor can be in signal communication with the controller 380 via wires and/or wireless communication such that the controller 380 can receive a signal from the sensor indicating that the trigger 128 has been moved into a first actuated position corresponding with the first distal position of cutting member 340. In various alternative embodiments, the encoder sensor can be configured to directly detect the displacement of the cutting member 340 via detectable members positioned on the cutting member 340, for example, wherein such an encoder sensor can be positioned within the handle 105 and/or shaft 108, for example.

Figure 7:
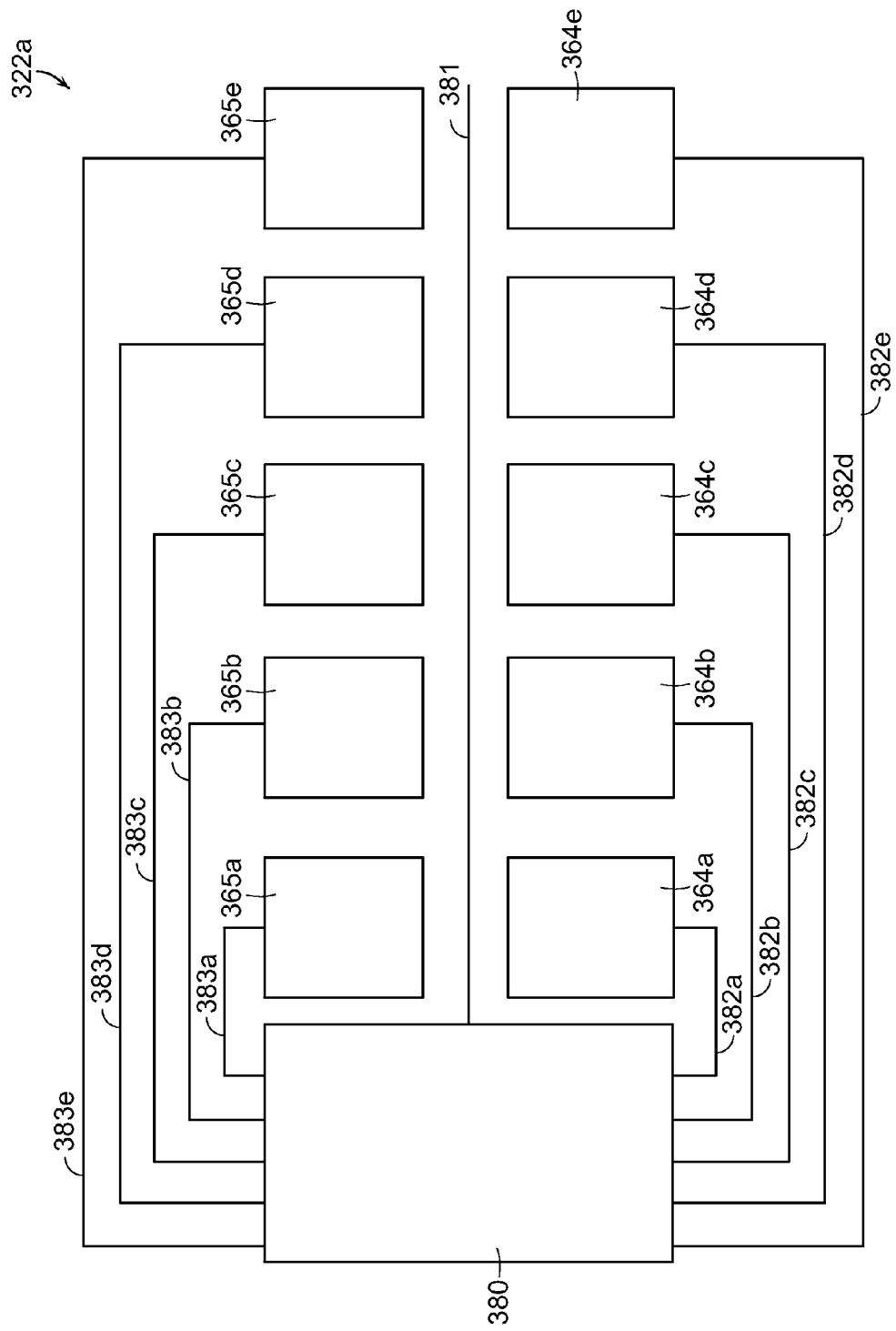
FIG. 7 is a schematic of the end effector of FIG. 5.

Once the controller 380 has received a signal from the encoder sensor that the trigger 128 has been moved into its first actuated position and that, correspondingly, the cutting member 340 is in its first distal position, the controller 380 can, referring now to FIG. 7, electrically couple first conductors 382a and 383a with the RF source. As illustrated in FIG. 7, the first conductors 382a and 383a are electrically coupled to the first electrodes 364a and 365a, respectively, such that current can flow through the conductors 382a, 383a and into the first electrodes 364a, 365a. In various embodiments, the controller 380 can comprise at least one microprocessor configured to receive one or more voltage inputs, wherein the microprocessor can comprise one or more gates or switches, for example, which, when switched by the voltage input from the sensor, permit the RF source to apply a voltage potential to the first pair of electrodes 364a, 365a. In various embodiments, further to the above, the controller 380 can be configured to operably couple the return electrodes 363 with a ground terminal, for example, of the RF source such that current can flow from the electrodes 364a, 365a, through the tissue positioned between jaws 322a, 322b, and into the return electrodes 363. As illustrated in FIG. 7, the return electrodes 363 are electrically coupled to the controller 380 via return conductor 381, for example.

Referring again to FIG. 8, the leading portions 355a, 355b of flanges 350a, 350b can be engaged with the electrodes 363 and the first pair of electrodes 364a and 365a in order to compress the tissue positioned between the tissue-contacting surfaces 362 and 389 as current is flowing between the first electrodes 384a, 365a and the electrodes 363. In such an arrangement, the current can flow through the tissue that is being compressed by the distal end of the cutting member 340. Furthermore, such an arrangement can assure that current does not flow through the tissue unless it has been properly compressed between the tissue-contacting surfaces 362 and 369 of the electrodes that will be treating the tissue. In various embodiments, the encoder sensor, the detectable element 109a, and the controller 380 of the surgical instrument can be configured such that the voltage potential from the RF source is applied to the first electrodes 364a, 365a at the same time that the leading portions 355a, 355b of cutting member 340 first engages electrodes 364a and 365a. More particularly, in at least one such embodiment, the voltage potential can be applied to the first electrodes 364a, 365a at the same time that the distal edge of leading portion 355a comes into contact with the proximal edges of electrodes 364a, 365a, for example. In certain embodiments, the surgical instrument can be configured such that the voltage potential from the RF source is applied to the first electrodes 364a, 365a only after the leading portions 355a, 355b have been fully engaged with the electrodes 364a, 365a, and 363. More particularly, in at least one such embodiment, the voltage potential can be applied to the first electrodes 364a, 365a at the same time that the distal edge of leading portion 355a is aligned with, is substantially aligned with, and/or passes, the distal edges of electrodes 364a, 365a, for example. As the reader will note, the cutting edge 351 is positioned proximally with respect to the leading portions 355a, 355b such that, in various embodiments, the cutting edge 351 may not transect the tissue between the electrodes 364a, 365a and 363 until after the tissue has been fully compressed and/or after the tissue has been at least partially welded.

Figure 6:
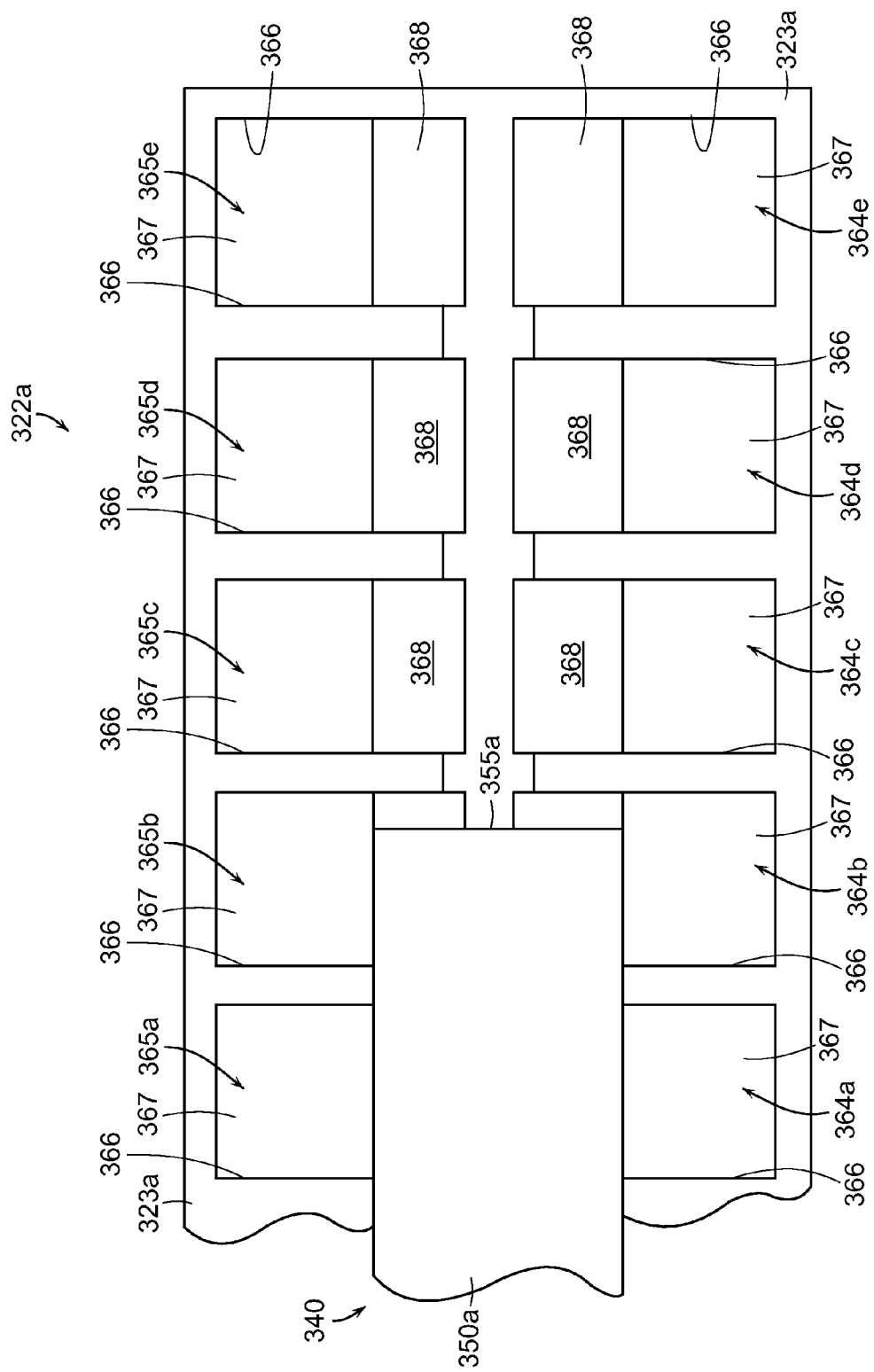
FIG. 6 is a top view of the end effector of FIG. 5 illustrated with components removed.

In various embodiments, further to the above, the trigger 128 can be moved into a second actuated position in order to move the cutting member 340 into a second distal position (FIG. 6). As the cutting member 340 is advanced, the cutting edge 351 can transect the tissue. In the second actuated position of cutting member 340, further to the above, the leading portions 355a, 355b of cutting member 340 can be engaged with a second pair of electrodes 364b, 365b and the return electrodes 363. Similar to the above, as a result, the leading portions 355a, 355b can compress the tissue positioned between the tissue-contacting surfaces of electrodes 364b, 365b and 363. In various embodiments, further to the above, the trigger 128 can comprise a second detectable member 109b which can be detected by the encoder sensor when the trigger 128 has been moved into its second actuated position and, correspondingly, the cutting member 340 has been moved into its second distal position. After the controller 380 has received a signal from the encoder sensor that the trigger 128 is in its second actuated position, similar to the above, the controller 380 can, referring now to FIG. 7, electrically couple second conductors 382b and 383b with the RF source. As illustrated in FIG. 7, the second conductors 382b and 383b are electrically coupled to the second electrodes 364b and 365b, respectively, such that current can flow through the second conductors 382b, 383b and into the second electrodes 364b, 365b. As described above, the controller 380 can be configured to operably couple the return electrodes 363 with a ground terminal, for example, of the RF source such that current can flow from the second electrodes 364b, 365b, through the tissue positioned between jaws 322a, 322b, and into the return electrodes 363. In various embodiments, the electrodes 363 and the return conductor 381 can be electrically coupled with the ground terminal of the RF supply throughout the operation of the surgical instrument.

In various embodiments, further to the above, the trigger 128 can be moved into a third actuated position in order to move the cutting member 340 into a third distal position (FIG. 5). As the cutting member 340 is advanced, the cutting edge 351 can transect the tissue. In the third actuated position of cutting member 340, further to the above, the leading portions 355a, 355b of cutting member 340 can be engaged with a third pair of electrodes 364c, 365c and the return electrodes 363. Similar to the above, as a result, the leading portions 355a, 355b can compress the tissue positioned between the tissue-contacting surfaces of electrodes 364c, 365c and 363. In various embodiments, further to the above, the trigger 128 can comprise a third detectable member 109c which can be detected by the encoder sensor when the trigger 128 has been moved into its third actuated position and, correspondingly, the cutting member 340 has been moved into its third distal position. After the controller 380 has received a signal from the encoder sensor that the trigger 128 is in its third actuated position, similar to the above, the controller 380 can, referring now to FIG. 7, electrically couple third conductors 382c and 383c with the RF source. As illustrated in FIG. 7, the third conductors 382c and 383c are electrically coupled to the third electrodes 364c and 365c, respectively, such that current can flow through the third conductors 382c, 383c and into the third electrodes 364c, 365c. As described above, the controller 380 can be configured to operably couple the return electrodes 363 with a ground terminal, for example, of the RF source such that current can flow from the third electrodes 364c, 365c, through the tissue positioned between jaws 322a, 322b, and into the return electrodes 363.

In various embodiments, further to the above, the trigger 128 can be moved into a fourth actuated position in order to move the cutting member 340 into a fourth distal position. As the cutting member 340 is advanced, the cutting edge 351 can transect the tissue. In the fourth actuated position of cutting member 340, further to the above, the leading portions 355a, 355b of cutting member 340 can be engaged with a fourth pair of electrodes 364d, 365d and the return electrodes 363. Similar to the above, as a result, the leading portions 355a, 355b can compress the tissue positioned between the tissue-contacting surfaces of electrodes 364d, 365d and 363. In various embodiments, further to the above, the trigger 128 can comprise a fourth detectable member 109d which can be detected by the encoder sensor when the trigger 128 has been moved into its fourth actuated position and, correspondingly, the cutting member 340 has been moved into its fourth distal position. After the controller 380 has received a signal from the encoder sensor that the trigger 128 is in its fourth actuated position, similar to the above, the controller 380 can, referring now to FIG. 7, electrically couple fourth conductors 382d and 383d with the RF source. As illustrated in FIG. 7, the fourth conductors 382d and 383d are electrically coupled to the fourth electrodes 364d and 365d, respectively, such that current can flow through the fourth conductors 382d, 383d and into the fourth electrodes 364d, 365d. As described above, the controller 380 can be configured to operably couple the return electrodes 363 with a ground terminal, for example, of the RF source such that current can flow from the fourth electrodes 364d, 365d, through the tissue positioned between jaws 322a, 322b, and into the return electrodes 363.

In various embodiments, further to the above, the trigger 128 can be moved into a fifth actuated position in order to move the cutting member 340 into a fifth distal position. As the cutting member 340 is advanced, the cutting edge 351 can transect the tissue. In the fifth actuated position of cutting member 340, further to the above, the leading portions 355a, 355b of cutting member 340 can be engaged with a fifth pair of electrodes 364e, 365e and the return electrodes 363. Similar to the above, as a result, the leading portions 355a, 355b can compress the tissue positioned between the tissue-contacting surfaces of electrodes 364e, 365e and 363. In various embodiments, further to the above, the trigger 128 can comprise a fifth detectable member 109e which can be detected by the encoder sensor when the trigger 128 has been moved into its fifth actuated position and, correspondingly, the cutting member 340 has been moved into its fifth distal position. After the controller 380 has received a signal from the encoder sensor that the trigger 128 is in its fifth actuated position, similar to the above, the controller 380 can, referring now to FIG. 7, electrically couple fifth conductors 382e and 383e with the RF source. As illustrated in FIG. 7, the fifth conductors 382e and 383e are electrically coupled to the fifth electrodes 364e and 365e, respectively, such that current can flow through the fifth conductors 382e, 383e and into the fifth electrodes 364e, 365e. As described above, the controller 380 can be configured to operably couple the return electrodes 363 with a ground terminal, for example, of the RF source such that current can flow from the fifth electrodes 364e, 365e, through the tissue positioned between jaws 322a, 322b, and into the return electrodes 363.

As described above, a surgical instrument can comprise a plurality of conductors 382a-382e, 383a-383e, and 381 extending between the controller 380 and the electrodes 364a-364e, 365a-365e, and 363. In various embodiments, one or more of conductors 382a-382e, 383a-383e, and 381 can be comprised of insulated wires comprising a conductive material, such as a copper and/or aluminum core, for example, and a jacket comprised of an insulative material, such as polyvinylchloride, for example, surrounding the conductive core. In certain embodiments, one or more of conductors 382a-382e, 383a-383e, and 381 can be comprised of conductive materials extending through and/or embedded within the shaft of the surgical instrument, such as shaft 108, for example. In at least one such embodiment, each of the conductors 382a-382e, 383a-383e, and 381 can comprise an elongate metal member, such as a rod, for example, embedded in a plastic body, or spine, of the shaft, for example. In either event, the conductors 382a-382e, 383a-383e, and 381 can be electrically insulated from one another.

As described above, the handle of the surgical instrument can comprise, one, an encoder sensor positioned within the surgical instrument handle and, two, a plurality of detectable members positioned on the movable trigger, wherein the movement of trigger and the detectable members can be detected by the encoder sensor. In various alternative embodiments, the surgical instrument handle and/or shaft can comprise a plurality of sensors positioned and arranged to detect a detectable member positioned on the trigger and/or cutting member, for example. In at least one such embodiment, for example, the handle can comprise a first sensor configured to detect when the trigger has been moved into its first actuated position, a second sensor configured to detect when the trigger has been moved into its second actuated position, a third sensor configured to detect when the trigger has been moved into its third actuated position, a fourth sensor configured to detect when the trigger has been moved into its fourth actuated position, and a fifth sensor configured to detect when the trigger has been moved into its fifth actuated position, and so forth. In certain embodiments, the shaft can comprise a first sensor configured to detect when the firing member, or cutting member 340, has been moved into its first distal position, a second sensor configured to detect when the cutting member 340 has been moved into its second distal position, a third sensor configured to detect when the cutting member 340 has been moved into its third distal position, a fourth sensor configured to detect when the cutting member 340 has been moved into its fourth distal position, and a fifth sensor configured to detect when the cutting member 340 has been moved into its fifth distal position, and so forth. In either event, each of the sensors can be in signal communication with the controller 380 such that the controller 380 can receive an input signal, or signals, from the sensors in order to determine when to selectively permit a voltage potential to be applied to the electrodes 364a-364e and 365a-365e, for example.

As described above, the electrodes 364a-364e and 365a-365e can be activated, or polarized, sequentially. As each successive pair of electrodes is activated, the previous pair, or pairs, of electrodes can remain polarized. In at least one such embodiment, the first pair of electrodes 364a and 365a can remain polarized when the second pair of electrodes 364b and 365b are polarized, for example. Similarly, both the first and second pairs of electrodes can remain polarized when the third pair of electrodes 364c and 365c is polarized. Also, similarly, the first, second, and third pairs of electrodes can remain polarized when the fourth pair of electrodes 364d and 365d is polarized. Further, similarly, the first, second, third, and fourth pairs of electrodes can remain polarized when the fifth pair of electrodes 364e and 365e is polarized and so forth. In various embodiments, all of the electrodes 364a-364e and 365a-365e can remain polarized until the controller 380 electrically decouples the electrodes from the RF source at the same time, or at least substantially the same time, for example. In various embodiments, the activation, or the application of a voltage potential, to each successive pair of electrodes can occur simultaneously, or at least substantially simultaneously, with the deactivation of the previous pair of electrodes. In at least one such embodiment, for example, the controller 380 can be programmed to switch off the voltage potential to the first pair of electrodes 364a and 365a when the controller 380 switches on the voltage potential to the second pair of electrodes 364b and 365b. Similarly, the controller 380 can be programmed to switch off the voltage potential to the second pair of electrodes 364b and 365b when the controller 380 switches on the voltage potential to the third pair of electrodes 364c and 365c. Also, similarly, the controller 380 can be programmed to switch off the voltage potential to the third pair of electrodes 364c and 365c when the controller 380 switches on the voltage potential to the fourth pair of electrodes 364d and 365d. Further, similarly, the controller 380 can be programmed to switch off the voltage potential to the fourth pair of electrodes 364d and 365d when the controller 380 switches on the voltage potential to the fifth pair of electrodes 364e and 365e, and so forth. In certain embodiments, the controller 380 may be programmed such that the deactivation of the previous pair of electrodes lags the activation of the subsequent pair of electrodes. In at least one such embodiment, the previous pair of electrodes can be deactivated following a predetermined amount of time after the activation of the subsequent pair of electrodes, such as approximately 1 second, approximately 5 seconds, and/or approximately 10 seconds, for example. In certain embodiments, the previous pair of electrodes can be deactivated after the temperature of the previous pair of electrodes, and/or the tissue positioned thereagainst, has exceeded a predetermined temperature, such as approximately 110 degrees Celsius, approximately 120 degrees Celsius, and/or approximately 130 degrees Celsius, for example.

Although the embodiment of FIGS. 5-8 comprises five pairs of electrodes in the first jaw 322a, other embodiments are envisioned comprising more than or less than five pairs of electrodes. Furthermore, other embodiments are envisioned in which the first jaw comprises two or more sets of electrodes comprising two or more electrodes in each set which are polarized simultaneously. In addition, other embodiments are envisioned in which the second jaw of the end effector comprises electrodes which are polarized sequentially in addition to and/or in lieu of the sequentially polarized electrodes in the first jaw. Additionally, other embodiments are envisioned in which singular electrodes are polarized sequentially and are not part of pairs and/or sets of electrodes.

In various embodiments, as described above, current can flow from one electrode to another while passing through the tissue captured by the end effector of the surgical instrument. As also described above, the current passing through the tissue can heat the tissue. In various circumstances, however, the tissue may become overheated. In order to avoid such overheating, the electrodes of various surgical instruments can comprise materials which may no longer conduct current, or may conduct at least substantially less current, when the electrode materials have reached or exceeded a certain temperature. Stated another way, in at least one embodiment, the electrical resistance of the electrode material can increase with the temperature of the material and, in certain embodiments, the electrical resistance of the material can increase significantly when the material has reached or exceeded a certain transition, or switching, temperature. In various circumstances, such materials can be referred to as positive temperature coefficient, or PTC, materials. In at least some such PTC materials, the PTC material can be comprised of a first non-conductive material, or substrate, which has a high electrical resistance and, in addition, a second, conductive material, or particles, having a lower electrical resistance interdispersed throughout the substrate material. In at least one embodiment, the substrate material can comprise polyethylene and/or high-density polyethylene (HDPE), for example, and the conductive material can comprise carbon particles, for example. In any event, when the temperature of the PTC material is below its transition temperature, the conductive material can be present in the non-conductive material in a sufficient volumetric density such that the current can flow through the PTC material via the conductive particles. When the temperature of the PTC material has exceeded its transition temperature, the substrate, or non-conductive material may have sufficiently expanded and/or changed states such that the conductive particles are no longer sufficiently in contact with one another in order provide a sufficient path for the current to flow therethrough. Stated another way, the expansion and/or state change of the substrate material may cause the volumetric density of the conductive particles to fall below a sufficient volumetric density in order for current to be conducted therethrough, or at least substantially conducted therethrough. In various circumstances, as a result of the above, the PTC material may act as a circuit breaker which can prevent, or at least inhibit, additional energy from reaching the tissue being treated, that is, at least until the PTC material has cooled sufficiently and reached a temperature which is below the transition, or switching, temperature. At such point, the PTC material could begin to conduct current again.

Further to the above, describing a material as having a positive temperature coefficient of resistance (PTC) can mean that the resistance of the material increases as the temperature of the material increases. Many metal-like materials exhibit electrical conduction that has a slight positive temperature coefficient of resistance. In such metal-like materials, the PTC's variable resistance effect is characterized by a gradual increase in resistance that is linearly proportional to temperature—that is, a linear PTC effect. A "nonlinear" PTC effect can be exhibited by certain types of polymer matrices, or substrates, that are doped with conductive particles. These polymer PTC compositions can comprise a base polymer that undergoes a phase change or can comprise a glass transition temperature Tg such that the PTC composition has a resistance that increases sharply over a narrow temperature range (see FIG. 9).

Polymeric PTC material can consist of a crystalline or semi-crystalline polymer (e.g., polyethylene) that carries a dispersed filler of conductive particles, such as carbon powder or nickel particles, for example, therein. In use, a polymeric PTC material can exhibit temperature-induced changes in the base polymer in order to alter the electrical resistance of the polymer-particle composite. In a low temperature state, the crystalline structure of the base polymer can cause dense packing of the conductive particles (i.e., carbon) into its crystalline boundaries so that the particles are in close proximity and allow current to flow through the PTC material via these carbon "chains". When the PTC material is at a low temperature, numerous carbon chains form the conductive paths through the material. When the PTC material is heated to a selected level, or an over-current causes $I^2R$ heating (Joule heating) within the PTC material, the polymer base material may be elevated in temperature until it exceeds a phase transformation temperature. As the polymer passes through this phase transformation temperature, the crystalline structure can change to an amorphous state. The amorphous state can cause the conductive particles to move apart from each other until the carbon chains are disrupted and can no longer conduct current. Thus, the resistance of the PTC material increases sharply. In general, the temperature at which the base polymer transitions to its amorphous state and affects conductivity is called its switching temperature Ts. In at least one embodiment, the transition or switching temperature Ts can be approximately 120 degrees Celsius, for example. In any event, as long as the base polymer of the PTC material stays above its switching temperature Ts, whether from external heating or from an overcurrent, the high resistance state will remain. Reversing the phase transformation allows the conductive particle chains to reform as the polymer re-crystallizes to thereby restore multiple current paths, and a low resistance, through the PTC material. Conductive polymer PTC compositions and their use are disclosed in U.S. Pat. Nos. 4,237,441; 4,304,987; 4,545,926; 4,849,133; 4,910,389; 5,106,538; and 5,880,668, the entire disclosures of which are incorporated by reference herein.

As discussed above, in many embodiments, the conductive polymer PTC composition may comprise a base polymer, or substrate, and conductive elements dispersed in the base polymer. When describing properties of the base polymer of a PTC composition, it may be useful to further explain the terms glass transition temperature Tg and melting temperature Tm. A glass transition temperature Tg of a material may not be the same as a melting temperature Tm. A transition at Tm occurs in crystalline polymers when the polymer chains fall out of their crystalline phase, and become a disordered deformable or flowable media. A glass transition at Tg is a transition which occurs in amorphous polymers (i.e., polymers whose chains are not arranged in ordered crystals). A glass transition temperature (Tg) in a crystalline polymer may be defined as a temperature point where the polymer experiences a significant change in properties-such as a large change in Young's modulus (also known as modulus of elasticity), for example. In such circumstances, the Tg can comprise the temperature at which the polymer structure turns "rubbery" upon heating and "glassy" upon cooling. Crystalline polymers may also go through a stage of becoming leathery before becoming rubbery. There is a loss of stiffness (e.g., decreased modulus of elasticity) in both of these stages. Such crystalline polymers, or domains thereof, can comprise a sharp, defined melting point Tm. In contrast, an amorphous polymer can be structural below the glass transition temperature Tg and transition from being stiff to flowable (at its melting temperature Tm) over a wide temperature range.

The temperature-induced variable resistance of a polymer PTC composition when used in a current-limiting application can be based on an overall energy balance—and can be described by Equation (1) below. It may now be useful to describe the basic thermal/resistance properties of a PTC device comprising a polymeric PTC composition to explain how (i) highly non-linear PTC effects and (ii) rapid switching may be achieved in the PTC materials described herein.

$$m^*Cp(\Delta T/\Delta t)=I^2{}^*R-U^*(T-Ta)—\quad \text{Equation (1), wherein:}$$

m=mass of the PTC composition
Cp=specific heat capacity of the PTC composition (at a constant pressure)
$\Delta T$=change in temperature of the PTC composition
$\Delta t$=change in time
I=current flowing through the PTC composition
R=resistance of the PTC composition
U=overall heat-transfer coefficient
T=temperature of the PTC composition
Ta=ambient temperature In equation (1) above, the current flowing through the PTC composition generates heat at a rate equal to $I^2R$. All or some of this heat can be subtracted by interaction with the environment at a rate described by the term U*(T-Ta), depending on how the device or composition is configured for interaction with the environment. This portion of equation (1), i.e., U*(T-Ta), accounts for losses due to one or more of convection, conduction, and radiation heat transfers. Any heat not subtracted by environmental interaction raises the temperature of the PTC composition/device at a rate described by the term: m*Cp*($\Delta T/\Delta t$)—Equation (2). The reader will note that Equation (2) assumes that there is a uniform temperature across the polymeric PTC composition. In circumstances where this is not true, this portion of the equation can be adapted in order to account for such particularities. In any event, if the heat generated by the polymeric PTC composition and the heat subtracted to the operating environment are in balance, T/t goes to zero, and Equation (1) can be rewritten as: $I^2$*R-U*(T-Ta)—Equation (3). In various circumstances, under certain operating conditions, the heat generated within the PTC material and the heat lost by the PTC material to the environment can be in balance at a relatively low temperature such as, for example, Point A shown in FIG. 9. If the current flow (I) through the PTC composition increases and the ambient temperature remains constant, the heat generated by the PTC composition increases and, correspondingly, the temperature of the PTC composition also increases. In the event, however, that the increase in current is not too large and all the generated heat can be lost to the environment, the temperature and resistance of the PTC material may stabilize according to Equation (3) at a higher temperature, such as Point B in FIG. 9, for example.

Figure 9:
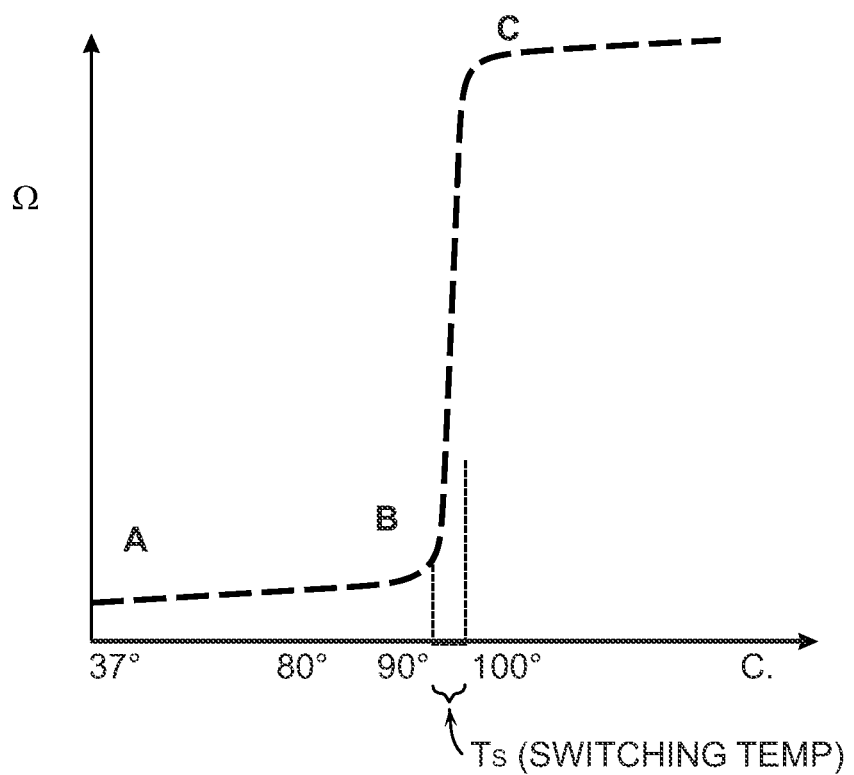
FIG. 9 is a diagram illustrating a temperature-resistance curve of a positive temperature coefficient material.

In various circumstances, if the ambient temperature surrounding the PTC material, or the temperature of an object engaged by the PTC material, increases instead of the current, the PTC material may stabilize according to Equation (3) at a slightly higher temperature (possibly again at Point B in FIG. 9). Point B in FIG. 9 can also be reached as a result of an increase in current (I) and an increase in ambient temperature Ta. In various circumstances, however, further increases in either or both of these conditions may cause the PTC material to reach a temperature Ts at which the resistance rapidly increases (e.g., from Point B to Point C in FIG. 9). At this stage, large increases in resistance occur with small changes in temperature. In FIG. 9, this occurs between Points B and C, and this vertical or "square" portion of the curve defines the operating region of the PTC composition in its tripped state. The large change in resistance causes a corresponding decrease in current flow in a circuit including or otherwise electrically coupled to the PTC composition. In various circumstances, the resistance, or impedance, can increase by approximately two orders of magnitude, for example, while, in other circumstances, the resistance, or impedance, can increase by approximately four orders of magnitude, for example. In certain circumstances, the change in the resistance, or impedance, can depend on the frequency of the current passing through the PTC material. In at least some circumstances, the resistance can increase by four orders of magnitude when the current is at Rf frequencies, for example, and two orders of magnitude when the current is below Rf frequencies, for example. In any event, because the temperature change between Points B and C in FIG. 9 is very small, the term (T-Ta) in Equation (3) can be replaced by the constant (Ts-Ta), wherein Ts is the current-limiting, or switching, temperature of the device. As a result of the above, Equation (1) can be rewritten as: $I^2*R=V^2/R=U*(Ts-Ta)$—Equation (4). Because U and (Ts-Ta) are now both constants, Equation (4) reduces to $I^2R$=constant; that is, the device now operates in a constant power state under these conditions. Expressing this constant power as $V^2/R$ emphasizes that, in the tripped state, the resistance of the PTC material is proportional to the square of the applied voltage. This relation holds until the composition/device resistance reaches the upper "square" region of the curve (Point C in FIG. 9).

For a PTC composition that has tripped, i.e., exceed its switch temperature, the PTC composition will remain in the tripped state and will remain substantially non-conductive as long as the applied voltage is high enough for the resulting $V^2/R$ to supply and/or exceed the U(Ts-Ta) loss. When the voltage is decreased to the point at which the U(Ts-Ta) loss can no longer be supplied to the PTC material, the PTC material will "reset" or return to its quiescent base resistance, such as points represented by Points A and/or B, for example. Various embodiments can comprise PTC materials that allow for a very rapid bi-directional switching (e.g., a small $\Delta t$) between Points B and C along the resistance-temperature curve of FIG. 9. Various embodiments can comprise PTC materials that exhibit a resistance-temperature curve with a high degree of "squareness" at its Ts (see FIG. 9), that is, the embodiment of the PTC material will plot an exceedingly rapid nonlinear PTC effect (e.g., a rapid increase in resistivity) in the range of a selected switching temperature Ts. A vertical, or an at least substantially vertical, curve at Ts can mean that the change from a base quiescent resistance to a maximum current-limiting resistance occurs over a very small temperature range.

From the following equation, it can be understood that switching time can be effectively reduced by altering the mass of the PTC composition. The switching time can generally be represented by Equation (5): $\Delta t=m*Cp*(Ts-Ta)/(I^2*R)$. By controlling one or more variables from Equation (5), various embodiments of PTC materials can provide one or both of reduced switching time and/or a square resistance-temperature curve. An exemplary embodiment of a conductive polymer composition/polymer composite which provides a greatly increased switching speed can utilize thermally insulative, low mass, yet electrically conductive dispersed nanospheres and/or microspheres. It has also been found that the embodiments of the above described polymer composite can provide a very low or minimum resistance in its initial quiescent state. At the same time, a polymer with thermally insulative, low mass conductive particles can provide for an increased Imax property, i.e., the maximum current the PTC composition can withstand without damage.

In various embodiments, further to the above, each of the electrodes 364a-364e and 365a-365e can be comprised of one or more PTC materials. In at least one embodiment, the cutting member 340 can be advanced from an initial position into its first distal position in which the cutting member 340 is in contact with electrodes 364a and 365a and in which the controller 380 can electrically couple the electrodes 364a and 365a with a power source. As the current flows through the electrodes 364a, 365a, further to the above, the temperature of the electrodes 364a, 365a can increase until the switching temperature of the PTC material comprising electrodes 364a, 365a is reached and/or exceeded thereby resulting in the current flowing through the electrodes 364a, 365a being switched, or at least substantially switched, off. In various embodiments, the cutting member 340 may not be advanced into its second distal position and into engagement with the second pair of electrodes 364b, 365b until the switching temperature of the first pair of electrodes 364a, 365a has been met and/or exceeded. After the switching temperature of the first pair of electrodes 364a, 365a has been met and/or exceeded, the cutting member 340 may be advanced into its second distal position in which the controller 380 can electrically couple the electrodes 364b, 365b with the power source. As the current flows through the electrodes 364b, 365b, further to the above, the temperature of the electrodes 364b, 365b can increase until the switching temperature of the PTC material comprising electrodes 364b, 365b is reached and/or exceeded thereby resulting in the current flowing through the electrodes 364b, 365b being switched, or at least substantially switched, off. In various embodiments, the cutting member 340 may not be advanced into its third distal position into engagement with the third pair of electrodes 364c, 365c until the switching temperature of the second pair of electrodes 364b, 365b has been met and/or exceeded. Likewise, the cutting member 340 may not be advanced into its fourth distal position until third electrodes 364c and 365c have reached and/or exceeded their switching temperature while the cutting member 340 may not be advanced into its fifth distal position until fourth electrodes 364d and 365d have reached and/or exceeded their switching temperature. Once the fifth electrodes 364e and 365e have reached and/or exceeded their switching temperature, in at least one embodiment, the cutting member 340 can be retracted.

In various embodiments, further to the above, the cutting member 340 can be advanced into engagement with a subsequent pair of electrodes without regard as to whether the switching temperature of the previous electrodes has been reached and/or exceeded. In certain embodiments, as described above, the cutting member 340 can be moved into its first distal position and the first pair of electrodes 364a and 365a can be electrically coupled with the power source. In various embodiments, the current flowing through the electrodes 364a, 365a can increase the temperature of the electrodes 364a, 365a and, whether or not the electrodes 364a, 365a have yet reached their switching temperature, the cutting member 340 can be advanced into its second distal position in which it is engaged with the second pair of electrodes 364b, 365b. When the cutting member 340 has been moved into its second distal position, the second pair of electrodes 364b and 365b can be electrically coupled with the power source as described above. In various embodiments, the controller 380 can be programmed to maintain the first electrodes 364a, 365a in electrical communication with the power source as the cutting member 340 is moved from its first distal position into its second distal position, third distal position, fourth distal position, and/or fifth distal position. In at least one such embodiment, the first electrodes 364a, 365a can conduct current therethrough until the switching temperature of the PTC material comprising the electrodes 364a, 365a has been reached and/or exceeded. Similarly, the second electrodes 364b and 365b can conduct current therethrough until the switching temperature of the PTC material comprising the electrodes 364b, 365b has been reached and/or exceeded. Also, similarly, the third electrodes 364c, 365c, the fourth electrodes 364d, 365d, and/or the fifth electrodes 364e, 365e can conduct current therethrough until the switching temperature of the PTC material comprising these electrodes has been reached and/or exceeded. In various circumstances, as a result, the electrodes 364a-364e, 365a-365e can be switched off independently of the distal advancement of the cutting member 340.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
    a handle comprising a trigger;
    a shaft extending from said handle, wherein said shaft comprises:
        a firing member operably coupled with said trigger, wherein said firing member is sequentially movable between an initial position, a first deployed position, and a second deployed position, and wherein an actuation of said trigger is configured to impart a firing motion to said firing member and move said firing member between said initial position and said first deployed position and between said first deployed position and said second deployed position;
        a first conductor;
        a second conductor; and
        a return conductor, wherein said return conductor is electrically insulated from said first conductor and said second conductor, and wherein said second conductor is electrically insulated from said first conductor;
    a cutting member operably coupled with said firing member;
    an end effector, comprising:
        a proximal end operably engaged with said shaft;
        a distal end;

a first jaw, comprising:
  a first electrode comprised of a positive temperature coefficient material, wherein said first conductor is electrically coupled with said first electrode; and
  a second electrode comprised of a positive temperature coefficient material, wherein said first electrode is positioned proximally with respect to said second electrode, and wherein said second conductor is electrically coupled with said second electrode; and
a second jaw, wherein one of said first jaw and said second jaw is movable relative to the other of said first jaw and said second jaw, wherein said second jaw further comprises a return electrode, and wherein said return conductor is electrically coupled to said return electrode; and
a controller configured to:
  electrically couple said first conductor with a power source when said firing member is moved into said first deployed position; and
  electrically couple said second conductor with a power source when said firing member is moved into said second deployed position.

2. The surgical instrument of claim 1, wherein said firing member further comprises:
  a proximal end operably coupled with said trigger;
  a first compression portion configured to engage said first jaw, wherein said first compression portion comprises a first distal end; and
  a second compression portion configured to engage said second jaw, wherein said second compression portion comprises a second distal end, wherein said cutting member extends between said first compression portion and said second compression portion, and wherein said first distal end and said second distal end are positioned distally with respect to said cutting member.

3. The surgical instrument of claim 2, wherein said first electrode and said second electrode define a compression slot configured to receive said first compression portion and a cutting slot configured to receive said cutting member.

4. The surgical instrument of claim 1, wherein said trigger is sequentially movable between an unactuated position, a first actuated position, and a second actuated position, and wherein said handle further comprises:
  a first sensor configured to detect when said trigger has been moved into said first actuated position, wherein said first sensor is in signal communication with said controller; and
  a second sensor configured to detect when said trigger has been moved into said second actuated position, wherein said second sensor is in signal communication with said controller.

5. The surgical instrument of claim 1, wherein said shaft further comprises:
  a first sensor configured to detect when said firing member has been moved into said first deployed position, wherein said first sensor is in signal communication with said controller; and
  a second sensor configured to detect when said firing member has been moved into said second deployed position, wherein said second sensor is in signal communication with said controller.

6. The surgical instrument of claim 1, wherein said handle further comprises said power source.

7. A surgical instrument, comprising:
a handle comprising a trigger;
a shaft extending from said handle, wherein said shaft comprises:
  a firing member operably coupled with said trigger, wherein said firing member is sequentially movable between an initial position, a first deployed position, and a second deployed position, and wherein an actuation of said trigger is configured to impart a firing motion to said firing member and move said firing member between said initial position and said first deployed position and between said first deployed position and said second deployed position;
  a first conductor;
  a second conductor; and
  a return conductor, wherein said return conductor is electrically insulated from said first conductor and said second conductor, and wherein said second conductor is electrically insulated from said first conductor;
a cutting member operably coupled with said firing member;
an end effector, comprising:
  a proximal end operably engaged with said shaft;
  a distal end;
  a first jaw, comprising:
    a first electrode comprised of a positive temperature coefficient material, wherein said first conductor is electrically coupled with said first electrode; and
    a second electrode comprised of a positive temperature coefficient material, wherein said first electrode is positioned proximally with respect to said second electrode, and wherein said second conductor is electrically coupled with said second electrode; and
  a second jaw, wherein one of said first jaw and said second jaw is movable relative to the other of said first jaw and said second jaw, wherein said second jaw further comprises a return electrode, and wherein said return conductor is electrically coupled to said return electrode; and
a controller configured to:
  electrically couple said first conductor with a power source when said firing member is moved into said first deployed position; and
  electrically couple said second conductor with a power source when said firing member is moved into said second deployed position,
wherein said shaft further comprises a third conductor, wherein said third conductor is electrically insulated from said first conductor, said second conductor, and said return conductor, wherein said first jaw further comprises a third electrode positioned distally with respect to said second electrode, wherein said third electrode is comprised of a positive temperature coefficient material, wherein said third conductor is electrically coupled with said third electrode, wherein said firing member is sequentially movable into a third deployed position after said second deployed position, and wherein said controller is configured to electrically couple said third conductor with a power source when said firing member is moved into said third deployed position.

8. A surgical instrument, comprising:
a handle comprising a trigger;
a shaft extending from said handle, wherein said shaft comprises:
  a firing member operably coupled with said trigger, wherein said firing member is sequentially movable between an initial position, a first deployed position, and a second deployed position, and wherein at least one actuation of said trigger is configured to impart a firing motion to said firing member and move said firing member between said initial position and said first deployed position and between said first deployed position and said second deployed position;
a first conductor; and
a second conductor, wherein said second conductor is electrically insulated from said first conductor;
a cutting member operably coupled with said firing member;
an end effector, comprising:
a proximal end operably engaged with said shaft;
a distal end;
a first jaw, comprising:
a first electrode comprised of a positive temperature coefficient material, wherein said first conductor is electrically coupled with said first electrode; and
a second electrode comprised of a positive temperature coefficient material, wherein said first electrode is positioned proximally with respect to said second electrode, and wherein said second conductor is electrically coupled with said second electrode; and
a second jaw, wherein one of said first jaw and said second jaw is movable relative to the other of said first jaw and said second jaw;
at least one sensor configured to detect when said firing member is in said first deployed position and said second deployed position; and
a microprocessor configured to:
electrically couple said first conductor with a power source when said firing member is moved into said first deployed position; and
electrically couple said second conductor with a power source when said firing member is moved into said second deployed position.

9. The surgical instrument of claim 8, wherein said firing member further comprises:
a proximal end operably coupled with said trigger;
a first compression portion configured to engage said first jaw, wherein said first compression portion comprises a first distal end; and
a second compression portion configured to engage said second jaw, wherein said second compression portion comprises a second distal end, wherein said cutting member extends between said first compression portion and said second compression portion, and wherein said first distal end and said second distal end are positioned distally with respect to said cutting member.

10. The surgical instrument of claim 9, wherein said first electrode and said second electrode define a compression slot configured to receive said first compression portion and a cutting slot configured to receive said cutting member.

11. The surgical instrument of claim 8, wherein said trigger is sequentially movable between an unactuated position, a first actuated position, and a second actuated position, and wherein said at least one sensor comprises:
a first sensor configured to detect when said trigger has been moved into said first actuated position, wherein said first sensor is in signal communication with said microprocessor; and
a second sensor configured to detect when said trigger has been moved into said second actuated position, wherein said second sensor is in signal communication with said microprocessor.

12. The surgical instrument of claim 8, wherein said at least one sensor comprises:
a first sensor positioned within said shaft configured to detect when said firing member has been moved into said first deployed position, wherein said first sensor is in signal communication with said microprocessor; and
a second sensor positioned within said shaft configured to detect when said firing member has been moved into said second deployed position, wherein said second sensor is in signal communication with said microprocessor.

13. The surgical instrument of claim 8, wherein said handle further comprises said power source.

14. A surgical instrument, comprising:
a handle comprising a trigger;
a shaft extending from said handle, wherein said shaft comprises:
a firing member operably coupled with said trigger, wherein said firing member is sequentially movable between an initial position, a first deployed position, and a second deployed position, and wherein at least one actuation of said trigger is configured to impart a firing motion to said firing member and move said firing member between said initial position and said first deployed position and between said first deployed position and said second deployed position;
a first conductor; and
a second conductor, wherein said second conductor is electrically insulated from said first conductor;
a cutting member operably coupled with said firing member;
an end effector, comprising:
a proximal end operably engaged with said shaft;
a distal end;
a first jaw, comprising:
a first electrode comprised of a positive temperature coefficient material, wherein said first conductor is electrically coupled with said first electrode; and
a second electrode comprised of a positive temperature coefficient material, wherein said first electrode is positioned proximally with respect to said second electrode, and wherein said second conductor is electrically coupled with said second electrode; and
a second jaw, wherein one of said first jaw and said second jaw is movable relative to the other of said first jaw and said second jaw;
at least one sensor configured to detect when said firing member is in said first deployed position and said second deployed position; and
a microprocessor configured to:
electrically couple said first conductor with a power source when said firing member is moved into said first deployed position; and
electrically couple said second conductor with a power source when said firing member is moved into said second deployed position,
wherein said shaft further comprises a third conductor, wherein said third conductor is electrically insulated from said first conductor and said second conductor, wherein said first jaw further comprises a third electrode positioned distally with respect to said second electrode, wherein said third electrode is comprised of a positive temperature coefficient material, wherein said third conductor is electrically coupled with said third electrode, wherein said firing member is sequentially movable into a third deployed position after said second deployed position, and wherein said microprocessor is configured to electrically couple said third conductor with a power source when said firing member is moved into said third deployed position.

15. A surgical instrument, comprising:
a handle comprising a trigger sequentially movable between an unactuated position, a first actuated position, and a second actuated position;
a shaft extending from said handle, wherein said shaft comprises:
  a firing member operably coupled with said trigger, wherein said firing member is sequentially movable between an initial position, a first deployed position, and a second deployed position, and wherein at least one actuation of said trigger is configured to impart a firing motion to said firing member and move said firing member between said initial position and said first deployed position and between said first deployed position and said second deployed position;
  a first conductor; and
  a second conductor, wherein said second conductor is electrically insulated from said first conductor;
a cutting member operably coupled with said firing member;
an end effector, comprising:
  a proximal end operably engaged with said shaft;
  a distal end;
  a first jaw, comprising:
    a first electrode, wherein said first conductor is electrically coupled with said first electrode; and
    a second electrode, wherein said first electrode is positioned proximally with respect to said second electrode, and wherein said second conductor is electrically coupled with said second electrode; and
  a second jaw, wherein one of said first jaw and said second jaw is movable relative to the other of said first jaw and said second jaw; and
detection means for detecting the position of one of said trigger and said firing member; and
operating means for electrically coupling said first conductor with a power source when one of said trigger is moved into said first actuated position and said firing member is moved into said first deployed position, and for electrically coupling said second conductor with a power source when one of said trigger is moved into said second actuated position and said firing member is moved into said second deployed position.

16. The surgical instrument of claim 15, wherein said firing member further comprises:
a proximal end operably coupled with said trigger;
a first compression portion configured to engage said first jaw, wherein said first compression portion comprises a first distal end; and
a second compression portion configured to engage said second jaw, wherein said second compression portion comprises a second distal end, wherein said cutting member extends between said first compression portion and said second compression portion, and wherein said first distal end and said second distal end are positioned distally with respect to said cutting member.

17. The surgical instrument of claim 16, wherein said first electrode and said second electrode define a compression slot configured to receive said first compression portion and a cutting slot configured to receive said cutting member.

18. The surgical instrument of claim 15, wherein said detection means comprises:
a first sensor configured to detect when said trigger has been moved into said first actuated position, wherein said first sensor is in signal communication with said operating means; and
a second sensor configured to detect when said trigger has been moved into said second actuated position, wherein said second sensor is in signal communication with said operating means.

19. The surgical instrument of claim 15, wherein said detection means comprises:
a first sensor positioned within said shaft configured to detect when said firing member has been moved into said first deployed position, wherein said first sensor is in signal communication with said operating means; and
a second sensor positioned within said shaft configured to detect when said firing member has been moved into said second deployed position, wherein said second sensor is in signal communication with said operating means.

20. The surgical instrument of claim 15, wherein said handle further comprises said power source.

21. A surgical instrument, comprising:
a handle comprising a trigger sequentially movable between an unactuated position, a first actuated position, and a second actuated position;
a shaft extending from said handle, wherein said shaft comprises:
  a firing member operably coupled with said trigger, wherein said firing member is sequentially movable between an initial position, a first deployed position, and a second deployed position, and wherein at least one actuation of said trigger is configured to impart a firing motion to said firing member and move said firing member between said initial position and said first deployed position and between said first deployed position and said second deployed position;
  a first conductor; and
  a second conductor, wherein said second conductor is electrically insulated from said first conductor;
a cutting member operably coupled with said firing member;
an end effector, comprising:
  a proximal end operably engaged with said shaft;
  a distal end;
  a first jaw, comprising:
    a first electrode, wherein said first conductor is electrically coupled with said first electrode; and
    a second electrode, wherein said first electrode is positioned proximally with respect to said second electrode, and wherein said second conductor is electrically coupled with said second electrode; and
  a second jaw, wherein one of said first jaw and said second jaw is movable relative to the other of said first jaw and said second jaw;
detection means for detecting the position of one of said trigger and said firing member; and
operating means for electrically coupling said first conductor with a power source when one of said trigger is moved into said first actuated position and said firing member is moved into said first deployed position, and for electrically coupling said second conductor with a power source when one of said trigger is moved into said second actuated position and said firing member is moved into said second deployed position, wherein said shaft further comprises a third conductor, wherein said third conductor is electrically insulated from said first conductor and said second conductor, wherein said first jaw further comprises a third electrode positioned distally with respect to said second electrode, wherein said third conductor is electrically coupled with said third electrode, wherein said firing member is sequentially movable into a third deployed position after said second deployed position, and wherein said operating means is configured to electrically couple said third conductor with a power source when said firing member is moved into said third deployed position.

* * * * *